(12) United States Patent
Bartels et al.

(10) Patent No.: US 9,695,126 B2
(45) Date of Patent: Jul. 4, 2017

(54) FUNGICIDE PYRAZOLE CARBOXAMIDES DERIVATIVES

(71) Applicant: BAYER INTELLECTUAL PROPERTY GMBH, Monheim (DE)

(72) Inventors: Guenter Bartels, Burgwedel (DE); Angela Becker, Dusseldorf (DE); Juergen Benting, Leichlingen (DE); Christoph-Andreas Braun, Dusseldorf (DE); Peter Dahmen, Neuss (DE); Philippe Desbordes, Lyons (FR); Christophe Dubost, Charbonnieres-les-Bains (FR); Stephanie Gary, Champagne-au-Mont-d'Or (FR); Ulrich Gorgens, Ratingen (DE); Hiroyuki Hadano, Shimotsuke (JP); Benoit Hartmann, Sainte-Foy-les-Lyon (FR); Thomas Knobloch, Chatillon d'Azergues (FR); Marc Kosten, Weyhe (DE); Norbert Lui, Odenthal (DE); Ruth Meissner, Leverkusen (DE); Sergiy Pazenok, Solingen (DE); Rachel Rama, Lyons (FR); Arnd Voerste, Cologne (DE); Ulrike Wachendorff-Neumann, Neuwied (DE)

(73) Assignee: BAYER INTELLECTUAL PROPERTY GMBH, Monheim (DE)

(*) Notice: Subject to any disclaimer, the term of this patent is extended or adjusted under 35 U.S.C. 154(b) by 0 days.

(21) Appl. No.: 15/188,164

(22) Filed: Jun. 21, 2016

(65) Prior Publication Data

US 2016/0297766 A1    Oct. 13, 2016

Related U.S. Application Data

(62) Division of application No. 14/166,773, filed on Jan. 28, 2014, now Pat. No. 9,398,767, which is a division of application No. 13/319,614, filed as application No. PCT/EP2010/056521 on May 21, 2010, now Pat. No. 8,772,266.

(60) Provisional application No. 61/286,176, filed on Dec. 14, 2009.

(30) Foreign Application Priority Data

May 15, 2009 (EP) .................................. 09356035
Nov. 19, 2009 (EP) .................................. 09356058

(51) Int. Cl.
| | | |
|---|---|---|
| C07D 231/16 | (2006.01) | |
| C07D 401/12 | (2006.01) | |
| A01N 55/00 | (2006.01) | |
| A01N 43/56 | (2006.01) | |
| C07F 7/08 | (2006.01) | |

(52) U.S. Cl.
CPC ........... *C07D 231/16* (2013.01); *A01N 43/56* (2013.01); *A01N 55/00* (2013.01); *C07D 401/12* (2013.01); *C07F 7/0812* (2013.01)

(58) Field of Classification Search
None
See application file for complete search history.

(56) References Cited

U.S. PATENT DOCUMENTS

| | | | |
|---|---|---|---|
| 5,223,526 A | 6/1993 | McLoughlin et al. | 514/406 |
| 5,675,016 A | 10/1997 | Gallenkamp et al. | 548/374.1 |
| 5,750,721 A | 5/1998 | Gallenkamp et al. | 548/374.1 |
| 8,324,133 B2 | 12/2012 | Gary et al. | 504/130 |
| 8,765,971 B2 | 7/2014 | Pazenok et al. | 548/366.1 |
| 2009/0306401 A1 | 12/2009 | Neeff et al. | 548/374.1 |
| 2010/0010048 A1 | 1/2010 | Gary | |
| 2010/0144785 A1 | 6/2010 | Desbordes | |
| 2010/0144817 A1 | 6/2010 | Desbordes | |
| 2010/0189584 A1 | 7/2010 | Desbordes | |
| 2010/0286221 A1 | 11/2010 | Mansfield | |
| 2011/0207940 A1 | 8/2011 | Pazenok et al. | |

FOREIGN PATENT DOCUMENTS

| | | |
|---|---|---|
| CN | 101175750 A | 5/2008 |
| CN | 102666492 B | 3/2016 |
| EP | 0776889 A1 | 6/1997 |
| JP | 7-501549 | 2/1995 |

(Continued)

OTHER PUBLICATIONS

International Search Report issued Jan. 12, 2010, in corresponding International Application No. PCT/EP2010/056521, published as WO 2010/130767 A3.

*Primary Examiner* — Kamal Saeed
(74) *Attorney, Agent, or Firm* — Morrison & Foerster LLP

(57) ABSTRACT

The present invention relates to pyrazole carboxamides derivatives of formula (1) wherein Y represents $CR^5$ or N, T represents S or O, X1 and X2 represent a chlorine or a fluorine atom, and Z1 represents a substituted or non-substituted cyclopropyl; Their process of preparation, their use as fungicide, and/or anti-mycotoxin active agents, and/or insecticide, and/or nematicide, particularly in the form of fungicide compositions, and methods for the control of phytopathogenic fungi, notably of plants, using these compounds or compositions.

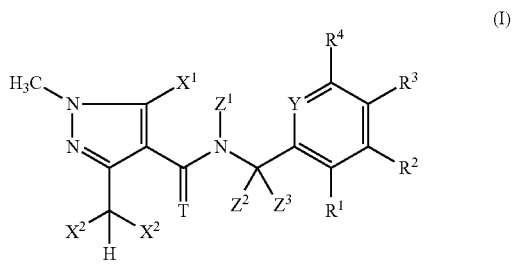

(I)

18 Claims, No Drawings

(56) References Cited

FOREIGN PATENT DOCUMENTS

| | | |
|---|---|---|
| JP | 09-176126 | 7/1997 |
| WO | WO 93/11117 | 6/1993 |
| WO | WO 2006/120224 | 11/2006 |
| WO | WO 2007/031212 | 3/2007 |
| WO | WO 2007/087906 | 8/2007 |
| WO | WO 2008/037789 A1 | 4/2008 |
| WO | WO 2009/016218 | 2/2009 |
| WO | WO 2009/016218 A2 | 2/2009 |
| WO | WO 2009/016219 | 2/2009 |
| WO | WO 2009/016219 A1 | 2/2009 |
| WO | WO 2009/016220 | 2/2009 |
| WO | WO 2009/016221 | 2/2009 |

FUNGICIDE PYRAZOLE CARBOXAMIDES DERIVATIVES

The present invention relates to pyrazole carboxamides derivatives, their process of preparation, their use as fungicide, and/or anti-mycotoxin active agents, and/or insecticide, and/or nematicide, particularly in the form of compositions, and methods for the control of phytopathogenic fungi, notably of plants, using these compounds or compositions.

International patent applications WO-2009/016219, WO-2007/087906, WO-2009/016220, WO-2009/016218 and WO-2008/037789 generically mention certain amides of the following formulas:

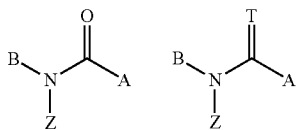

wherein A represents a carbo-linked, partially saturated or unsaturated, 5-membered heterocyclyl group that can be substituted, T represents S or N substituted derivatives, Z represents a (un)substituted cycloalkyl.

However, there is no disclosure or suggestion in these documents of any such derivative wherein A represent a 1-methyl-3-(difluoro or dichloro)methyl-5-(chloro or fluoro)-4-pyrazolyl.

International patent applications WO-2006/120224 generically mentions 2-pyridyl-methylene-carboxamide derivatives of formula:

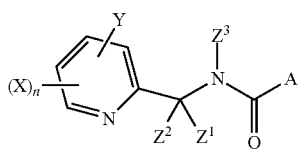

wherein A represents a carbo-linked 5-membered heterocyclyl group that can be substituted and $Z^3$ represents a substituted or non substituted $C_3$-$C_7$ cycloalkyl.

However, there is no disclosure of any derivatives according to the invention.

In international patent applications WO-2009/016221, certain amides are generically embraced in a broad disclosure of numerous compounds of the following formula:

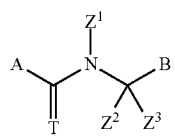

wherein A represents a carbo-linked, unsaturated or partially saturated, 5-membered heterocyclyl group that can be substituted and B represents an aromatic 5- or 6-membered, fused heterocyclyl ring comprising up to four heteroatoms, or an aromatic 6-membered fused carbocyclyl ring.

However there is no disclosure or suggestion in this document of any such derivative wherein B is a non fused aryl group.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining effectiveness at least equivalent to the already known compounds. We have now found a new family of compounds that possess the above mentioned effects or advantages.

Accordingly, the present invention provides derivatives of formula (I)

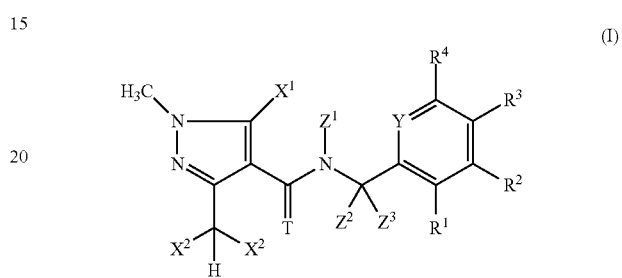

wherein
Y represents $CR^5$ or N;
T represents S or O;
$X^1$ and $X^2$ which can be the same or different, represent a chlorine or a fluorine atom;
$Z^1$ represents a non substituted cyclopropyl or a cyclopropyl substituted by up to 2 atoms or groups which can be the same or different and which can be selected in the list consisting of halogen atoms; cyano; $C_1$-$C_8$-alkyl; or $C_1$-$C_8$-halogenoalkyl comprising up to 9 halogen atoms which can be the same or different;
$Z^2$ and $Z^3$, which can be the same or different, represent a hydrogen atom; substituted or non substituted $C_1$-$C_8$-alkyl; substituted or non substituted $C_2$-$C_8$-alkenyl; substituted or non substituted $C_2$-$C_8$-alkynyl; cyano; isonitrile; nitro; a halogen atom; substituted or non substituted $C_1$-$C_8$-alkoxy; substituted or non substituted $C_2$-$C_8$-alkenyloxy; substituted or non substituted $C_2$-$C_8$-alkynyloxy; substituted or non substituted $C_3$-$C_7$-cycloalkyl; substituted or non substituted $C_1$-$C_8$-alkylsulfanyl; substituted or non substituted $C_1$-$C_8$-alkylsulfonyl; substituted or non substituted $C_1$-$C_8$-alkylsulfinyl amino; substituted or non substituted $C_1$-$C_8$-alkylamino; substituted or non substituted di-$C_1$-$C_8$-alkylamino; substituted or non substituted $C_1$-$C_8$-alkoxycarbonyl; substituted or non substituted $C_1$-$C_8$-alkylcarbamoyl; substituted or non substituted di-$C_1$-$C_8$-alkylcarbamoyl; or substituted or non substituted N—$C_1$-$C_8$-alkyl-$C_1$-$C_8$-alkoxycarbamoyl; or
$Z^3$ and $R^1$ together with the consecutive carbon atoms to which they are linked form a substituted or non substituted 5-, 6- or 7-membered, partly saturated, carbo- or hetero-cycle comprising up to 3 heteroatoms and $Z^2$ is as herein described; or
$Z^2$ and $Z^3$ together with the carbon atom to which they are linked form a substituted or non substituted $C_3$-$C_7$ cycloalkyl;
$R^1$, $R^2$, $R^3$, $R^4$ and $R^5$, which can be the same or different, represent a hydrogen atom; a halogen atom; nitro; cyano; isonitrile; hydroxyl; sulfanyl; amino; pentafluoro-$\Lambda^6$-sulfanyl; substituted or non substituted $C_1$-$C_8$-alkyl; $C_1$-$C_8$-halogenoalkyl comprising up to 9 halogen atoms which can be the same or different; substituted or non substituted $C_1$-$C_8$-alkylamino; substituted or non substituted di-$C_1$-$C_8$-alkylamino; substituted or non substituted $C_1$-$C_8$-alkoxy; $C_1$-$C_8$-halogenoalkoxy comprising up to 9 halogen atoms which can be the same or different; $C_1$-$C_8$-alkoxy-$C_1$-$C_8$-alkyl; substituted or non substituted $C_1$-$C_8$-alkylsulfanyl; $C_1$-$C_8$-halogenoalkylsulfanyl comprising up to 9 halogen atoms which can be the same or different; substituted or non substituted $C_2$-$C_8$-alkenyl; $C_2$-$C_8$-halogenoalkenyl comprising up to 9 halogen atoms which can be the same or different; substituted or non substituted $C_2$-$C_8$-alkynyl; $C_2$-$C_8$-halogenoalkynyl comprising up to 9 halogen atoms which can be the same or different; substituted or non substituted $C_2$-$C_8$-alkenyloxy; $C_2$-$C_8$-halogenoalkenyloxy comprising up to 9 halogen atoms which can be the same or different; substituted or non substituted $C_2$-$C_8$-alkynyloxy; $C_2$-$C_8$-halogenoalkynyloxy comprising up to 9 halogen atoms which can be the same or different; substituted or non substituted $C_3$-$C_7$-cycloalkyl; $C_3$-$C_7$-halogenocycloalkyl comprising up to 9 halogen atoms which can be the same or different; substituted or non substituted $C_3$-$C_7$-cycloalkyl-$C_1$-$C_8$-alkyl; substituted or non substituted $C_3$-$C_7$-cycloalkyl-$C_2$-$C_8$-alkenyl; substituted or non substituted $C_3$-$C_7$-cycloalkyl-$C_2$-$C_8$-alkynyl; substituted or non substituted $C_3$-$C_7$-cycloalkyl-$C_3$-$C_7$-cycloalkyl; substituted or non substituted $C_1$-$C_8$-alkyl-$C_3$-$C_7$-cycloalkyl; formyl formyloxy; formylamino; carboxy; carbamoyl; N-hydroxycarbamoyl; carbamate (hydroxyimino)-$C_1$-$C_8$-alkyl; substituted or non substituted $C_1$-$C_8$-alkylcarbonyl; $C_1$-$C_8$-halogenoalkylcarbonyl comprising up to 9 halogen atoms which can be the same or different; substituted or non substituted $C_1$-$C_8$-alkylcarbamoyl; substituted or non substituted di-$C_1$-$C_8$-alkylcarbamoyl; N-(substituted or non substituted $C_1$-$C_8$-alkyloxy)carbamoyl; substituted or non substituted $C_1$-$C_8$-alkoxycarbamoyl; N-(substituted or non substituted $C_1$-$C_8$-alkyl)-(substituted or non substituted $C_1$-$C_8$-alkoxy)-carbamoyl; substituted or non substituted $C_1$-$C_8$-alkoxycarbonyl; $C_1$-$C_8$-halogenoalkoxycarbonyl comprising up to 9 halogen atoms which can be the same or different; substituted or non substituted $C_1$-$C_8$-alkylaminocarbonyl; di-substituted or non substituted $C_1$-$C_8$-alkylaminocarbonyl; substituted or non substituted $C_1$-$C_8$-alkylcarbonyloxy; $C_1$-$C_8$-halogenoalkylcarbonyloxy comprising up to 9 halogen atoms which can be the same or different; substituted or non substituted $C_1$-$C_8$-alkylcarbonylamino; $C_1$-$C_8$-halogenoalkylcarbonylamino comprising up to 9 halogen atoms which can be the same or different; substituted or non substituted $C_1$-$C_8$-alkylaminocarbonyloxy; substituted or non substituted di-$C_1$-$C_8$-alkylaminocarbonyloxy; substituted or non substituted $C_1$-$C_8$-alkyloxycarbonyloxy; substituted or non substituted $C_1$-$C_8$-alkylsulfinyl; $C_1$-$C_8$-halogenoalkylsulfinyl comprising up to 9 halogen atoms which can be the same or different; substituted or non substituted $C_1$-$C_8$-alkylsulfonyl; $C_1$-$C_8$-halogenoalkylsulfonyl comprising up to 9 halogen atoms which can be the same or different; substituted or non substituted $C_1$-$C_8$-alkoxyimino; ($C_1$-$C_8$-alkoxyimino)-$C_1$-$C_8$-alkyl; substituted or non substituted ($C_1$-$C_8$-alkenyloxyimino)-$C_1$-$C_8$-alkyl; ($C_1$-$C_8$-alkynyloxyimino)-$C_1$-$C_8$-alkyl; a (benzyloxyimino)-$C_1$-$C_8$-alkyl; tri(substituted or non substituted $C_1$-$C_8$-alkyl)silyl; tri(substituted or non substituted $C_1$-$C_8$-alkyl)silyl-$C_1$-$C_8$-alkyl; benzyloxy which can be substituted by up to 5 groups Q; benzylsulfanyl which can be substituted by up to 5 groups Q; benzylamino which can be substituted by up to 5 groups Q; aryl which can be substituted by up to 7 groups Q; aryloxy which can be substituted by up to 7 groups Q; arylamino which can be substituted by up to 7 groups Q; arylsulfanyl which can be substituted by up to 7 groups Q; aryl-$C_1$-$C_8$alkyl which can be substituted by up to 7 groups Q; aryl-$C_2$-$C_8$-alkenyl which can be substituted by up to 7 groups Q; aryl-$C_2$-$C_8$-alkynyl which can be substituted by up to 7 groups Q; pyridinyl which can be substituted by up to 4 groups Q; pyridinyloxy which can be substituted by up to 4 groups Q; aryl-$C_3$-$C_7$-cycloalkyl which can be substituted by up to 7 groups Q; or Two vicinal substituents R together with the consecutive carbon atoms to which they are linked form a substituted or non substituted 5- or 6-membered, saturated, carbo- or hetero-cycle comprising up to 3 heteroatoms and the other substituents R are as herein-described; or $R^1$ and $Z^3$ together with the consecutive carbon atoms to which they are linked form a substituted or non substituted 5-, 6- or 7-membered, partly saturated, carbo- or hetero-cycle comprising up to 3 heteroatoms, and $R^2$ to $R^5$ are as herein-described;

Q, which can be the same or different, represents a halogen atom; cyano; nitro; $C_1$-$C_8$-alkyl; $C_1$-$C_8$-alkoxy; $C_1$-$C_8$-alkylsulfanyl; $C_1$-$C_8$-halogenoalkyl comprising up to 9 halogen atoms which can be the same or different; $C_1$-$C_8$-halogenoalkoxy comprising up to 9 halogen atoms which can be the same or different; tri($C_1$-$C_8$)alkylsilyl or tri($C_1$-$C_8$)alkylsilyl-$C_1$-$C_8$-alkyl;

with the provisio that when Y represents N, and T represents O, and $Z^1$ represents a cyclopropyl group, and $R^1$ represents a chlorine atom, and $R^3$ represents a trifluoromethyl group, and $R^2$ and $R^4$ represent a hydrogen atom, then a least one of the substituent $Z^2$ or $Z^3$ is not a hydrogen atom, as well as salts, N-oxydes, metallic complexes, metalloidic complexes and optically active or geometric isomers thereof.

Unless indicated otherwise, a group or a substituent that is substituted according to the invention can be substituted by one or more of the following groups or atoms: a halogen atom; nitro; hydroxyl; cyano; isonitrile; amino; thio; a pentafluoro-$X^6$-sulfanyl group formyl; formyloxy; formylamino; carbamoyl; N-hydroxycarbamoyl; carbamate (hydroxyimino)-$C_1$-$C_6$-alkyl; $C_1$-$C_8$-alkyl; a tri($C_1$-$C_8$-alkyl) silyl; $C_3$-$C_8$-cycloalkyl; $C_1$-$C_8$-halogenoalkyl having 1 to 5 halogen atoms; a $C_3$-$C_8$-halogenocycloalkyl having 1 to 5 halogen atoms; $C_2$-$C_8$-alkenyl; $C_2$-$C_8$-alkynyl; $C_2$-$C_8$-alkenyloxy; $C_2$-$C_8$-alkynyloxy; $C_1$-$C_8$-alkylamino; di-$C_1$-$C_8$-alkylamino; $C_1$-$C_8$-alkoxy; $C_1$-$C_8$-halogenoalkoxy having 1 to 5 halogen atoms; $C_1$-$C_8$-alkylsulfanyl; $C_1$-$C_8$-halogenoalkylsulfanyl having 1 to 5 halogen atoms; $C_2$-$C_8$-alkenyloxy; $C_2$-$C_8$-halogenoalkenyloxy having 1 to 5 halogen atoms; $C_3$-$C_8$-alkynyloxy; $C_3$-$C_8$-halogenoalkynyloxy having 1 to 5 halogen atoms; $C_1$-$C_8$-alkylcarbonyl $C_1$-$C_8$-halogenoalkylcarbonyl having 1 to 5 halogen atoms; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_8$-alkoxycarbamoyl; $C_1$-$C_8$-alkoxycarbonyl; $C_1$-$C_8$-halogenoalkoxycarbonyl having 1 to 5 halogen atoms; $C_1$-$C_8$-alkylcarbonyloxy; $C_1$-$C_8$-halogenoalkylcarbonyloxy having 1 to 5 halogen atoms; $C_1$-$C_8$-alkylcarbonylamino; $C_1$-$C_8$-halogenoalkylcarbonylamino having 1 to 5 halogen atoms; $C_1$-$C_8$-alkylaminocarbonyloxy; di-$C_1$-$C_8$-alkylaminocarbonyloxy; $C_1$-$C_8$-alkyloxycarbonyloxy; $C_1$-$C_8$-alkylsulfanyl; $C_1$-$C_8$-halogenoalkylsulfanyl having 1 to 5 halogen atoms; $C_1$-$C_8$-alkylsulfinyl; $C_1$-$C_8$-halogenoalkylsulfinyl having 1 to 5 halogen atoms; $C_1$-$C_8$-alkylsulphonyl; $C_1$-$C_8$-halogenoalkylsulfonyl having 1 to 5 halogen atoms $C_1$-$C_8$-alkylaminosulfamoyl; di-$C_1$-$C_8$-alkylaminosulfamoyl; ($C_1$-$C_6$-alkoxyimino)-$C_1$-$C_6$-alkyl; ($C_1$-$C_6$-alkenyloxyimino)-$C_1$-$C_6$-alkyl; ($C_1$-$C_6$-alkynyloxyimino)-$C_1$-$C_6$-alkyl; 2-oxopyrrolidin-1-yl; (benzyloxyimino)-$C_1$-$C_6$-alkyl; $C_1$-$C_8$-alkoxyalkyl; $C_1$-$C_8$-halogenoalkoxyalkyl having 1 to 5 halogen atoms; benzyloxy; benzylsulfanyl benzylamino; aryloxy; arylsulfanyl or arylamino.

Any of the compounds according to the invention can exist as one or more stereoisomers depending on the number of stereogenic units (as defined by the IUPAC rules) in the compound. The invention thus relates equally to all the stereoisomers, and to the mixtures of all the possible stereoisomers, in all proportions. The stereoisomers can be separated according to the methods that are known per se by the man ordinary skilled in the art.

According to the invention, the following generic terms are generally used with the following meanings:
- halogen means fluorine, chlorine, bromine or iodine;
- heteroatom can be nitrogen, oxygen or sulphur;
- any alkyl, alkenyl or alkynyl group can be linear or branched;
- the term "aryl" means phenyl or naphthyl, optionally substituted;
- In the case of an amino group or the amino moiety of any other amino-comprising group, substituted by two substituents that can be the same or different, the two substituents together with the nitrogen atom to which they are linked can form a heterocyclyl group, preferably a 5- to 7-membered heterocyclyl group, that can be substituted or that can include other hetero atoms, for example a morpholino or piperidinyl group.

Preferred compounds of formula (I) according to the invention are those wherein Y represents $CR^5$.

Other preferred compounds of formula (I) according to the invention are those wherein Y represents N.

Other preferred compounds of formula (I) according to the invention are those wherein T represents O.

Other preferred compounds of formula (I) according to the invention are those wherein $X^1$ represents a fluorine atom.

Other preferred compounds of formula (I) according to the invention are those wherein $X^2$ represents a fluorine atom.

Other preferred compounds of formula (I) according to the invention are those wherein $Z^1$ represents a non substituted cyclopropyl.

Other preferred compounds of formula (I) according to the invention are those wherein $Z^2$ and $Z^3$ independently represent a hydrogen atom or a methyl.

More preferred compounds of formula (I) according to the invention are those wherein $Z^2$ represents a hydrogen atom and $Z^3$ represents a hydrogen atom or a methyl.

Other preferred compounds of formula (I) according to the invention are those wherein $R^1$, $R^2$, $R^3$, $R^4$ and $R^5$, which can be the same or different, represent a hydrogen atom; a halogen atom; substituted or non substituted $C_1$-$C_8$-alkyl; $C_1$-$C_8$-halogenoalkyl comprising up to 9 halogen atoms which can be the same or different; substituted or non substituted $C_3$-$C_0$-cycloalkyl; tri($C_1$-$C_8$-alkyl)silyl; or substituted or non substituted $C_1$-$C_8$-alkylsulfanyl.

More preferred compounds of formula (I) according to the invention are those wherein the substituent $R^1$ represents a halogen atom; $C_1$-$C_8$-alkyl; $C_1$-$C_8$-halogenoalkyl comprising up to 9 halogen atoms which can be the same or different; $C_3$-$C_7$-cycloalkyl; tri($C_1$-$C_8$-alkyl)silyl or $C_1$-$C_8$-halogenoalkylsulfanyl comprising up to 9 halogen atoms which can be the same or different. Other more preferred compounds of formula (I) according to the invention are those wherein the substitutents $R^1$ and $R^5$, which can be the same or different, represent a halogen atom; $C_1$-$C_8$-alkyl; $C_1$-$C_8$-halogenoalkyl comprising up to 9 halogen atoms which can be the same or different; $C_3$-$C_0$-cycloalkyl; tri($C_1$-$C_8$-alkyl)silyl or $C_1$-$C_8$-halogenoalkylsulfanyl comprising up to 9 halogen atoms which can be the same or different.

The above mentioned preferences with regard to the substituents of the compounds of formula (I) according to the invention can be combined in various manners, either individually, partially or entirely. These combinations of preferred features thus provide sub-classes of compounds according to the invention. Examples of such sub-classes of preferred compounds according to the invention can combine:

preferred features of T with preferred features of one or more $X^1$, $X^2$, Y, $Z^1$ to $Z^3$, and $R^1$ to $R^5$;

preferred features of $X^1$ with preferred features of one or more T, $X^2$, Y, $Z^1$ to $Z^3$, and $R^1$ to $R^5$;

preferred features of $X^2$ With preferred features of one or more T, $X^1$, Y, $Z^1$ to $Z^3$, and $R^1$ to $R^5$;

preferred features of Y with preferred features of one or more T, $X^1$, $X^2$, $Z^1$ to $Z^3$, and $R^1$ to $R^5$;

preferred features of $Z^1$ with preferred features of one or more T, $X^1$, $X^2$, Y, $Z^2$, $Z^3$, and $R^1$ to $R^5$;

preferred features of $Z^2$ with preferred features of one or more T, $X^1$, $X^2$, Y, $Z^1$, $Z^3$, and $R^1$ to $R^5$;

preferred features of $Z^3$ with preferred features of one or more T, $X^1$, $X^2$, Y, $Z^1$, $Z^2$, and $R^1$ to $R^5$;

preferred features of $R^1$ with preferred features of one or more T, $X^1$, $X^2$, Y, $Z^1$ to $Z^3$, and $R^2$ to $R^5$;

preferred features of $R^2$ with preferred features of one or more T, $X^1$, $X^2$, Y, $Z^1$ to $Z^3$, $R^1$, and $R^3$ to $R^5$;

preferred features of $R^3$ with preferred features of one or more T, $X^1$, $X^2$, Y, $Z^1$ to $Z^3$, $R^1$, $R^2$, $R^4$, and $R^5$;

preferred features of $R^4$ with preferred features of one or more T, $X^1$, $X^2$, Y, $Z^1$ to $Z^3$, $R^1$ to $R^3$, and $R^5$;

preferred features of $R^5$ with preferred features of one or more T, $X^1$, $X^2$, Y, $Z^1$ to $Z^3$, and $R^1$ to $R^4$;

In these combinations of preferred features of the substituents of the compounds according to the invention, the said preferred features can also be selected among the more preferred features of each of T, $X^1$, $X^2$, Y, $Z^1$ to $Z^3$, and $R^1$ to $R^5$; so as to form most preferred subclasses of compounds according to the invention.

The present invention also relates to a process for the preparation of compounds of formula (I). Thus according to a further aspect of the present invention there is provided a process P1 for the preparation of compound of formula (Ia) as herein-defined for which T represents a oxygen atom, as illustrated by the following reaction scheme:

Process P1
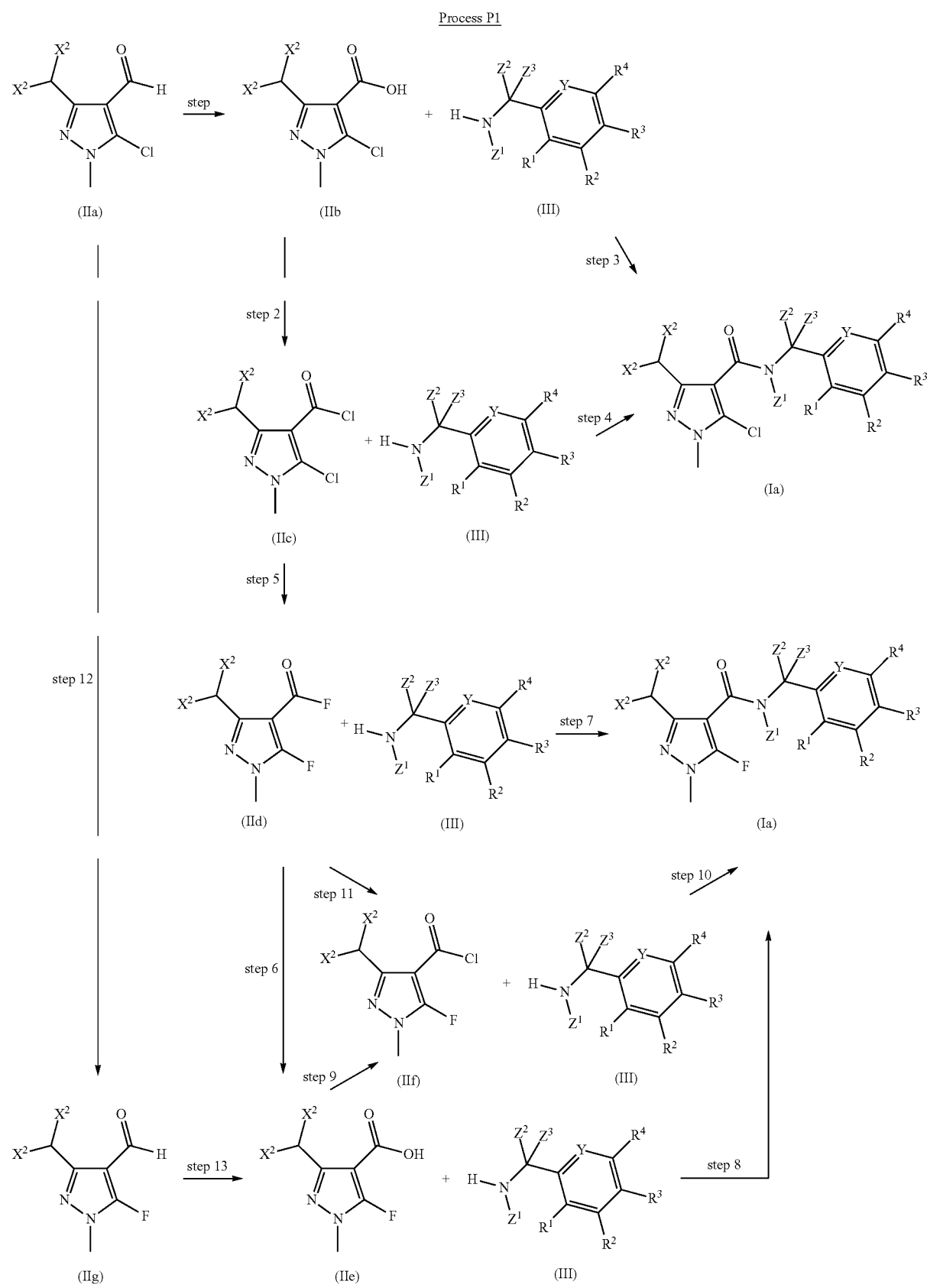

wherein $Z^1$, $Z^2$, $Z^3$, $R^1$, $R^2$, $R^3$, $R^4$, Y and $X^2$ are as herein-defined;

5-chloro-3-(difluoromethyl)-1-methyl-1H-pyrazole-4-carbaldehyde is known from WO-2004/014138 (reference example 35).

N-Cyclopropylamines of formula are known (WO-2008/037789, WO-2007/087906, WO-2006/120224 and WO-2009/016218) or can be prepared by known methods Step 1 and 13 of process P1 is performed in the presence of an oxidant, and if appropriate in the presence of a solvent.

Steps 2 and 9 of process P1 are performed in the presence of acid halide, and if appropriate in the presence of a solvent.

Steps 4, 7 and 10 of process P1 are performed in the presence of an acid binder, and if appropriate in the presence of a solvent.

Steps 3 and 8 of process P1 are performed in the presence of a condensing agent, and if appropriate in the presence of a solvent.

Step 5 and 12 of process P1 is performed in the presence of a fluorinating agent, and if appropriate in the presence of a solvent.

Step 11 of process P1 is performed in the presence of a chlorinating agent and a lewis acid, and if appropriate in the presence of a solvent.

According to a further aspect of the present invention there is provided a process P2 for the preparation of compound of formula (Ia) as herein-defined for which T represent a oxygen atom, as illustrated by the following reaction scheme:

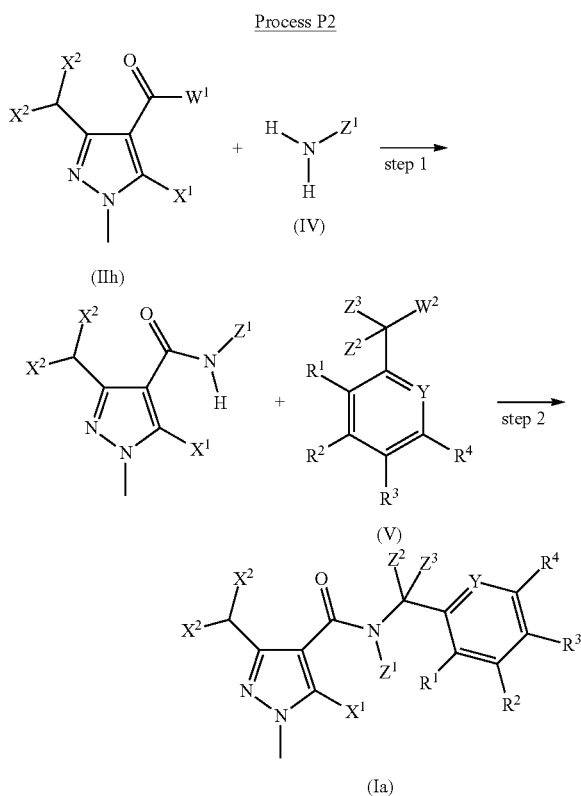

wherein $Z^1$, $Z^2$, $Z^3$, Y, $R^1$, $R^2$, $R^3$, $R^4$, $X^1$ and $X^2$ are as herein-defined;

$W^1$ represents a halogen atom or a hydroxyl;

$W^2$ represents a halogen or a leaving group such as tosylate, mesylate or triflate group.

Pyrazoles derivatives of formula (IIh) may be prepared according to process P1. N-cyclopropylamines of formula (IV) and methylene derivatives of formula (V) are known or may be prepared by known methods.

Step 1 of process P2 is performed in the presence of an acid binder or a condensing agent, and if appropriate in the presence of a solvent.

Step 2 of process P2 is performed in the presence of a solvent and if appropriate in the presence of an acid binder.

According to a further aspect of the present invention there is provided a process P3 for the preparation of compound of formula (Ib) as herein-defined for which T represent a sulfur atom, as illustrated by the following reaction scheme:

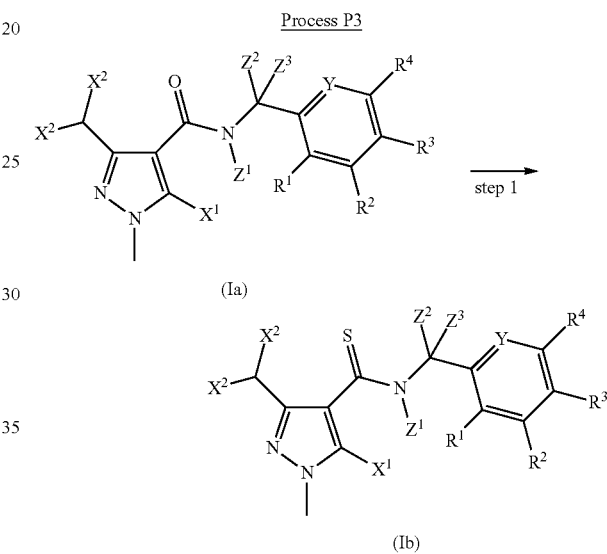

wherein $Z^1$, $Z^2$, $Z^3$, Y, $R^1$, $R^2$, $R^3$, $R^4$, $X^1$ and $X^2$ are as herein-defined;

Step 1 of process P3 is performed in the presence of a thionating agent and if appropriate in the presence of an acid binder and if appropriate in the presence of solvent.

Suitable oxidants for carrying out step 1 or 13 of process P1 according to the invention are in each case all inorganic and organic oxidant which are customary for such reactions. Preference is given to using benzyltriethylammonium permanganate; bromine; chlorine; m-chloroperbenzoic acid; chromic acid; chromium (VI) oxide; hydrogen peroxide; hydrogen peroxide-boron trifluoride; hydrogen peroxide-urea; 2-hydroxyperoxyhexafluoro-2-propanol; Iodine; oxygen-platinum catalyst, perbenzoic acid; peroxyacetyl nitrate; potassium permanganate; potassium ruthenate; pyridinium dichromate; ruthenium (VIII) oxide; silver (I) oxide; silver (II) oxide; silver nitrite; sodium chlorite; sodium hypochlorite; 2,2,6,6-tetramethylpiperidin-1-oxyl.

Suitable acid halides for carrying out steps 2 and 9 of process P1 according to the invention are in each case all organic or inorganic acid halides which are customary for such reactions. Preference is given to using notably phosgene, phosphorous trichloride, phosphorous pentachloride, phosphorous trichloride oxide; thionyl chloride; or carbon tetrachloride-triphenylphosphine.

Suitable acid binder for carrying out steps 4, 7 and 10 of process P1, steps 1 and 2 of process P2 and process P3 according to the invention are in each case all inorganic and organic bases which are customary for such reactions. Preference is given to using alkaline earth metal, alkali metal hydride, alkali metal hydroxides or alkali metal alkoxydes, such as sodium hydroxide, sodium hydride, calcium hydroxide, potassium hydroxide, potassium tert-butoxide or other ammonium hydroxide, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, and also ternary amines, such as trimethylamine, triethylamine, tributylamine, N,N-dimethylaniline, di-isopropyl-ethylamine, pyridine, methylethylpyridine, methylimidazole, N-methylpiperidine, N,N-dimethylaminopyridine, diazabicyclooctane (DABCO), diazabicyclononene (DBN) or diazabicycloundecene (DBU). It is also possible to work in the absence of an acid binder or to employ an excess of the amine component, so that it simultaneously acts as acid binder agent.

Suitable condensing agent for carrying out steps 3 and 8 of process P1 and step 1 of process P2 according to the invention are in each case all condensing agents which are customary for such reactions. Preference is given to using carbodiimides, such as N,N'-dicyclohexylcarbodiimide (DCC) or other customary condensing agents, notably phosphorous pentoxide, polyphosphoric acid, N,N'-carbonyldi-imidazole, 2-ethoxy-N-ethoxycarbonyl-1,2-dihydroquinoline (EEDQ), triphenylphosphine/tetrachloromethane or bromo-tripyrrolidinophosphonium-hexafluorophosphate.

Suitable fluorinating agent for carrying out step 5 or 12 of process P1 according to the invention is in each case all fluorinating agents which are customary for such reactions. Preference is given to using cesium fluoride; potassium fluoride; potassium fluoride-calcium difluoride; tetrabutylammonium fluoride.

Suitable chlorination agent for carrying out step 11 of process P1 according to the invention is in each case all chlorination agents agents which are customary for such reactions (WO-2007/062776). Preference is given to using tetrachlorosilane/aluminium trichloride, aluminium trichloride.

Suitable thionating agents for carrying out process P3 according to the invention can be sulphur (S), sulfhydric acid (H2S), sodium sulfide (Na2S), sodium hydrosulfide (NaHS), boron trisulfide ($B_2S_3$), bis (diethylaluminium) sulfide (($AlEt_2)_2S$), ammonium sulfide (($NH_4)_2S$), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in J. Chem. Soc. Perkin 1, (2001), 358.

Suitable solvents for carrying out steps 1 to 13 of process P1, steps 1 and 2 of process P2 and process P3 according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, cyclopentyl methylether, diisopropyl ether, methyl t-butyl ether, methyl t-amyl ether, dioxane, tetrahydrofuran, 2-methyl tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

When carrying out steps 1 to 13 of process P1 and steps 1 and 2 of process P2 according to the invention, the reaction temperatures can independently be varied within a relatively wide range. Generally, processes according to the invention are carried out at temperatures between 0° C. and 160° C., preferably between 10° C. and 120° C. A way to control the temperature for the processes according to the invention is to use the micro-waves technology.

Steps 1 to 13 of process P1 and steps 1 and 2 of process P2 according to the invention are generally independently carried out under atmospheric pressure. However, in each case, it is also possible to operate under elevated or reduced pressure.

When carrying out step 1 or 13 of process P1 according to the invention, generally 1 mol or other an excess of the oxidant is employed per mole of aldehyde of formula (IIa) or (IIg). It is also possible to employ the reaction components in other ratios.

When carrying out carrying out steps 2 and 9 of process P1 to the invention, generally 1 mol or other an excess of the acid halides is employed per mole of acid of formula (IIb) or (IIe). It is also possible to employ the reaction components in other ratios.

When carrying out steps 4, 7 and 10 of process P1 and step 1 and 2 of process P2 according to the invention generally 1 mol or other an excess of the acid binder is employed per mole of acid halides of formula (IIc), (IId) or (IIf). It is also possible to employ the reaction components in other ratios.

When carrying out process P3 according to the invention, generally 1 mol or other an excess of the acid binder is employed per mole of compound (Ia). It is also possible to employ the reaction components in other ratios.

When carrying out steps 3 and 8 of process P1 and step 1 of process P2 according to the invention generally 1 mol or other an excess of the condensing agent is employed per mole of acid of formula (IIb) and (IIe). It is also possible to employ the reaction components in other ratios.

When carrying out step 5 or 12 of process P1 according to the invention, generally 2 moles or other an excess of the fluorinating agent is employed per mole of chlorinated compound of formula (IIa) or (IIc). It is also possible to employ the reaction components in other ratios.

When carrying out step 11 of process P1 according to the invention, generally 0.2-0.3 mol of chlorinating agent is employed per mole of acid fluoride formula (IId). It is also possible to employ the reaction components in other ratios.

Work-up is carried out by customary methods. Generally, the reaction mixture is treated with water and the organic phase is separated off and, after drying, concentrated under reduced pressure. If appropriate, the remaining residue can, be freed by customary methods, such as chromatography, recrystallization or distillation, from any impurities that may still be present.

Compounds according to the invention can be prepared according to the above described process. It will nevertheless be understood that, on the basis of his general knowledge and of available publications, the skilled worker will be able to adapt these processes according to the specifics of each of the compounds according to the invention that is desired to be synthesized.

Still in a further aspect, the present invention relates to compounds of formula (II) useful as intermediate compounds or materials for the process of preparation according to the invention.

The present invention thus provides:

compounds of formula (IIb)

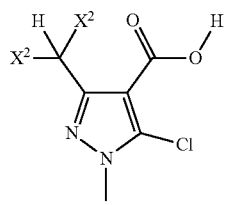

(IIb)

wherein $X^2$ represents a chlorine or a fluorine atom, preferably a fluorine atom;

compounds of formula (IIc')

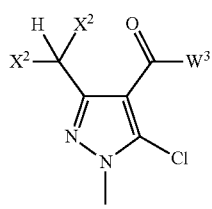

(IIc')

wherein $X^2$ represents a chlorine or a fluorine atom, preferably a fluorine atom and $W^3$ represent a halogen atom preferably a chlorine atom;

compounds of formula (IId)

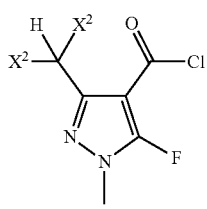

(IId)

wherein $X^2$ represents a chlorine or a fluorine atom, preferably a fluorine atom.

compounds of formula (IIe)

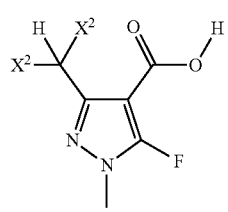

(IIe)

wherein $X^2$ represents a chlorine or a fluorine atom, preferably a fluorine atom.

compounds of formula (IIf)

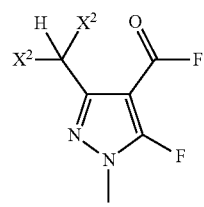

(IIf)

wherein $X^2$ represents a chlorine or a fluorine atom, preferably a fluorine atom.

compounds of formula (IIg)

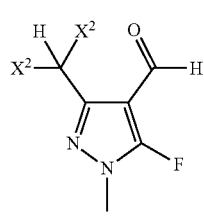

(IIg)

wherein $X^2$ represents a chlorine or a fluorine atom, preferably a fluorine atom.

In a further aspect, the present invention also relates to a composition, particularly a fungicide composition, comprising an effective and non-phytotoxic amount of an active compound of formula (I).

The expression "effective and non-phytotoxic amount" means an amount of composition according to the invention that is sufficient to control or destroy the fungi, and/or insects, and/or nematicides, and/or weeds present or liable to appear on or around the crops, and that does not entail any appreciable symptom of phytotoxicity for the said crops. Such an amount can vary within a wide range depending on the target, particularly fungus, to be controlled, the type of crop, the climatic conditions and the compounds included in the composition according to the invention. This amount can be determined by systematic field trials, that are within the capabilities of a person skilled in the art.

Thus, according to the invention, there is provided a composition, particularly a fungicide composition, comprising, as an active ingredient, an effective amount of a compound of formula (I) as herein defined and an agriculturally acceptable support, carrier or filler.

According to the invention, the term "support" denotes a natural or synthetic, organic or inorganic compound with that the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants.

Mention can be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds comprising sulphate, sulphonate and phosphate functions. The presence of at least one surfactant is generally essential when the active compound and/or the inert support are water-insoluble and when the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive, that complies with the usual formulation techniques.

In general, the composition according to the invention can contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions that are ready to be applied to the plant or seed to be treated by means of a suitable device, such as a spraying or dusting device, but also concentrated commercial compositions that must be diluted before application to the crop.

The compounds according to the invention can also be mixed with one or more insecticide, fungicide, bactericide, attractant, acaricide or pheromone active substance or other compounds with biological activity. The mixtures thus obtained have normally a broadened spectrum of activity. The mixtures with other fungicide compounds are particularly advantageous.

Examples of suitable fungicide mixing partners can be selected in the following lists:
(1) Inhibitors of the ergosterol biosynthesis, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifine (65472-88-0), (1.33) nuarimol (63284-71-9), (1.34) oxpoconazole (174212-12-5), (1.35) paclobutrazol (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl)cycloheptanol (129586-32-9), (1.61) methyl 1-(2,2-dimethyl-2,3-dihydro-1H-inden-1-yl)-1H-imidazole-5-carboxylate (111323-95-0), (1.62) N'-{5-(difluoromethyl)-2-methyl-4-[3-(trimethylsilyl)propoxy]phenyl}-N-ethyl-N-methyl-imidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl] 1H-imidazole-1-carbothioate (111226-71-2).
(2) inhibitors of the respiratory chain at complex I or II, for example (2.1) bixafen (581809-46-03), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) furametpyr (123572-88-3), (2.9) furmecyclox (60568-05-0), (2.10) isopyrazam (mixture of syn-epimeric racemate 1RS,4SR,9RS and anti-epimeric racemate 1RS,4SR,9SR) (881685-58-1), (2.11) isopyrazam (anti-epimeric racemate 1RS,4SR,9SR), (2.12) isopyrazam (anti-epimeric enantiomer 1R,4S,9S), (2.13) isopyrazam (anti-epimeric enantiomer 1S,4R,9R), (2.14) isopyrazam (syn epimeric racemate 1RS,4SR,9RS), (2.15) isopyrazam (syn-epimeric enantiomer 1R,4S,9R), (2.16) isopyrazam (syn-epimeric enantiomer 1S,4R,9S), (2.17) mepronil (55814-41-0), (2.18) oxycarboxin (5259-88-1), (2.19) penflufen (494793-67-8), (2.20) penthiopyrad (183675-82-3), (2.21) sedaxane (874967-67-6), (2.22) thifluzamide (130000-40-7), (2.23) 1-methyl-N-[2-(1,1,2,2-tetrafluoroethoxy)phenyl]-3-(trifluoromethyl)-1H-pyrazole-4-carboxamide, (2.24) fluxapyroxad (907204-31-3), (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N -[1-(2,4-dichlorophenyl)-1-methoxypropan-2-yl]-3-(difluoromethyl)-1-methyl-1H-pyrazole-4-carboxamide, and salts thereof.
(3) inhibitors of the respiratory chain at complex III, for example (3.1) amisulbrom (348635-87-0), (3.2) azoxystrobin (131860-33-8), (3.3) cyazofamid (120116-88-3), (3.4) dimoxystrobin (141600-52-4), (3.5) enestroburin (238410-11-2) (known from WO 2004/058723), (3.6) famoxadone (131807-57-3) (known from WO 2004/058723), (3.7) fenamidone (161326-34-7) (known from WO 2004/058723), (3.8) fluoxastrobin (361377-29-9) (known from WO 2004/058723), (3.9) kresoxim-methyl (143390-89-0) (known from WO 2004/058723), (3.10) metominostrobin (133408-50-1) (known from WO 2004/058723), (3.11) orysastrobin (189892-69-1) (known from WO 2004/058723), (3.12) picoxystrobin (117428-22-5) (known from WO 2004/058723), (3.13) pyraclostrobin (175013-18-0) (known from WO 2004/058723), (3.14) pyrametostrobin (915410-70-7) (known from WO 2004/058723), (3.15) pyraoxystrobin (862588-11-2) (known from WO 2004/058723), (3.16) pyribencarb (799247-52-2) (known from WO 2004/058723), (3.17) trifloxystrobin (141517-21-7) (known from WO 2004/058723), (3.18) (2E)-2-(2-{[6-(3-chloro-2-methylphenoxy)-5-fluoropyrimidin-4-yl]oxy}phenyl)-2-(methoxyimino)-N-methylethanamide (known from WO 2004/058723), (3.19) (2E)-2-(methoxyimino)-N-methyl-2-(2-{[({(1E)-1-[3-(trifluoromethyl)phenyl]ethylidene}amino)oxy]methyl}phenyl)ethanamide (known from WO 2004/058723) and salts thereof, (3.20) (2E)-2-(methoxyimino)-N-methyl-2-{2-[(E)-({1-[3-(trifluoromethyl)phenyl]ethoxy}imino)methyl]phenyl}ethanamide (158169-73-4), (3.21) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.22) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.23) 2-chloro-N-(1,1,3-trimethyl-2,3-dihydro-1H-inden-4-yl)pyridine-3-carboxamide (119899-14-8), (3.24) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.25) methyl (2E)-2-{2-[({cyclopropyl[(4-methoxyphenyl)imino]methyl}sulfanyl)methyl]phenyl}-3-methoxyprop-2-enoate (149601-03-6), (3.26) N-(3-ethyl-3,5,5-trimethylcyclohexyl)-3-(formylamino)-2-hydroxybenzamide (226551-21-9), (3.27) 2-{2-[(2,5-dimethylphenoxy)methyl]phenyl}-2-methoxy-N-methylacetamide (173662-97-0), (3.28) (2R)-2-{2-[(2,5-dimethylphenoxy)methyl]phenyl}-2-methoxy-N-methylacetamide (394657-24-0) and salts thereof.

(4) Inhibitors of the mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolide (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3) and (4.14) 3-chloro-5-(6-chloropyridin-3-yl)-6-methyl-4-(2,4,6-trifluorophenyl)pyridazine (1002756-87-7) and salts thereof.

(5) Compounds capable to have a multisite action, like for example (5.1) bordeaux mixture (8011-63-0), (5.2) captafol (2425-06-1), (5.3) captan (133-06-2) (known from WO 02/12172), (5.4) chlorothalonil (1897-45-6), (5.5) copper hydroxide (20427-59-2), (5.6) copper naphthenate (1338-02-9), (5.7) copper oxide (1317-39-1), (5.8) copper oxychloride (1332-40-7), (5.9) copper(2+) sulfate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (2234562), (5.24) maneb (12427-38-2), (5.25) metiram (9006-42-2), (5.26) metiram zinc (9006-42-2), (5.27) oxine-copper (10380-28-6), (5.28) propamidine (104-32-5), (5.29) propineb (12071-83-9), (5.30) sulphur and sulphur preparations including calcium polysulphide (7704-34-9), (5.31) thiram (137-26-8), (5.32) tolylfluanid (731-27-1), (5.33) zineb (12122-67-7), (5.34) ziram (137-30-4) and salts thereof.

(6) Compounds capable to induce a host defence, like for example (6.1) acibenzolar-S-methyl (135158-54-2), (6.2) isotianil (224049-04-1), (6.3) probenazole (27605-76-1) and (6.4) tiadinil (223580-51-6).

(7) Inhibitors of the amino acid and/or protein biosynthesis, for example (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7) and (7.7) pyrimethanil (53112-28-0).

(8) Inhibitors of the ATP production, for example (8.1) fentin acetate (900-95-8), (8.2) fentin chloride (639-58-7), (8.3) fentin hydroxide (76-87-9) and (8.4) silthiofam (175217-20-6).

(9) Inhibitors of the cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of the lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Inhibitors of the melanine biosynthesis, for example (11.1) carpropamid (104030-54-8), (11.2) diclocymet (139920-32-4), (11.3) fenoxanil (115852-48-7), (11.4) phthalide (27355-22-2), (11.5) pyroquilon (57369-32-1) and (11.6) tricyclazole (41814-78-2).

(12) Inhibitors of the nucleic acid synthesis, for example (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Inhibitors of the signal transduction, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Compounds capable to act as an uncoupler, like for example (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds like for example (15.1) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.2) 1-(4-methoxyphenoxy)-3,3-dimethylbutan-2-yl 1H-imidazole-1-carboxylate (111227-17-9), (15.3) 2,3,5,6-tetrachloro-4-(methylsulfonyl)pyridine (13108-52-6), (15.4) 2,3-dibutyl-6-chlorothieno[2,3-d]pyrimidin-4(3H)-one (221451-58-7), (15.5) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.6) 2-butoxy-6-iodo-3-propyl-4H-chromen-4-one, (15.7) 2-phenylphenol and salts (90-43-7), (15.8) 3,4,5-trichloropyridine-2,6-dicarbonitrile (17824-85-0), (15.9) 3-[5-(4-chlorophenyl)-2,3-dimethyl-1,2-oxazolidin-3-yl]pyridine, (15.10) 3-chloro-5-(4-chlorophenyl)-4-(2,6-difluorophenyl)-6-methylpyridazine, (15.11) 4-(4-chlorophenyl)-5-(2,6-difluorophenyl)-3,6-dimethylpyridazine, (15.12) 5-amino-1,3,4-thiadiazole-2-thiol, (15.13) 5-chloro-N'-phenyl-N'-(prop-2-yn-1-yl)thiophene-2-sulfonohydrazide (134-31-6), (15.14) 5-methyl-6-octyl[1,2,4]triazolo[1,5-a]pyrimidin-7-amine, (15.15) ametoctradin (865318-97-4), (15.16) benthiazole (21564-17-0), (15.17) bethoxazin (163269-30-5), (15.18) capsimycin (70694-08-5), (15.19) carvone (99-49-0), (15.20) chinomethionat (2439-01-2), (15.21) chlazafenone (688046-61-9), (15.22) cufraneb (11096-18-7), (15.23) cyflufenamid (180409-60-3), (15.24) cymoxanil (57966-95-7), (15.25) cyprosulfamide (221667-31-8), (15.26) dazomet (533-74-4), (15.27) debacarb (62732-91-6), (15.28) dichlorophen (97-23-4), (15.29) diclomezine (62865-36-5), (15.30) difenzoquat (43222-48-6), (15.31) difenzoquat methylsulphate (43222-48-6), (15.32) diphenylamine (122-39-4), (15.33) ecomate, (15.34) ethyl (2Z)-3-amino-2-cyano-3-phenylprop-2-enoate, (15.35) flumetover (154025-04-4), (15.36) fluoroimide (41205-21-4), (15.37) flusulfamide (106917-52-6), (15.38) flutianil (304900-25-2), (15.39) fosetyl-aluminium (39148-24-8), (15.40) fosetyl-calcium, (15.41) fosetyl-sodium (39148-16-8), (15.42) hexachlorobenzene (118-74-1), (15.43) irumamycin (81604-73-1), (15.44) methasulfocarb (66952-49-6), (15.45) methyl isothiocyanate (556-61-6), (15.46) metrafenone (220899-03-6), (15.47) mildiomycin (67527-71-3), (15.48) N-(4-chlorobenzyl)-3-[3-methoxy-4-(prop-2-yn-1-yloxy)phenyl]propanamide, (15.49) N-[(4-chlorophenyl)(cyano)methyl]-3-[3-methoxy-4-(prop-2-yn-1-yloxy)phenyl]propanamide, (15.50) N-[(5-bromo-3-chloropyridin-2-yl)methyl]-2,4-dichloropyridine-3-carboxamide, (15.51) N-[1-(5-bromo-3-chloropyridin-2-yl)ethyl]-2,4-dichloropyridine-3-carboxamide, (15.52) N-[1-(5-bromo-3-chloropyridin-2-yl)ethyl]-2-fluoro-4-iodopyridine-3-carboxamide, (15.53) N-{(E)-[(cyclopropylmethoxy)imino][6-(difluoromethoxy)-2,3-difluorophenyl]methyl}-2-phenylacetamide, (15.54) N-{(Z)-[(cyclopropylmethoxy)imino][6-(difluoromethoxy)-2,3-difluorophenyl]methyl}-2-phenylacetamide (221201-92-9), (15.55) natamycin (7681-93-8), (15.56) nickel dimethyldithiocarbamate (15521-65-0), (15.57) nitrothal-isopropyl (10552-74-6), (15.58) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.59) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.60) octhilinone (26530-20-1), (15.61) oxamocarb (917242-12-7), (15.62) oxyfenthiin (34407-87-9), (15.63) pentachlorophenol and salts (87-86-5), (15.64) pentyl {6-[({[(1-methyl-1H-tetrazol-5-yl)(phenyl)methylidene]amino}oxy)methyl]pyridin-2-yl}carbamate, (15.65) phenazine-1-carboxylic acid, (15.66) phenothrin, (15.67) phosphorous acid and its salts (13598-36-2), (15.68) propamocarb-fosetylate, (15.69) propanosine-sodium (88498-02-6), (15.70) proquinazid (189278-12-4), (15.71) pyrrolnitrine (1018-71-9) (known from EP-A 1 559 320), (15.72) quinolin-8-ol (134-31-6), (15.73) quinolin-8-ol sulfate (2:1) (134-31-6), (15.74) fenpyrazamine (473798-59-3), (15.75) tebufloquin (376645-78-2), (15.76) tecloftalam (76280-91-6), (15.77) tolnifanide (304911-98-6), (15.78) triazoxide (72459-58-6), (15.79) trichlamide (70193-21-4), (15.80) zarilamid (84527-51-5) and salts thereof.

(16) Further compounds like for example (2.27) 1-methyl-3-(trifluoromethyl)-N-[2'-(trifluoromethyl)biphenyl-2-yl]-1H-pyrazole-4-carboxamide, (2.28) N-(4'-chlorobiphenyl-2-yl)-3-(difluoromethyl)-1-methyl-1H-pyrazole-4-carboxamide, (2.29) N-(2',4'-dichlorobiphenyl-2-yl)-3-(difluoromethyl)-1-methyl-1H-pyrazole-4-carboxamide, (2.30) 3-(difluoromethyl)-1-methyl-N-[4'-(trifluoromethyl)biphenyl-2-yl]-1H-pyrazole-4-carboxamide, (2.31) N-(2',5'-difluorobiphenyl-2-yl)-1-methyl-3-(trifluoromethyl)-1H-pyrazole-4-carboxamide, (2.32) 3-(difluoromethyl)-1-methyl-N-[4'-(prop-1-yn-1-yl)biphenyl-2-yl]-1H-pyrazole-4-carboxamide (known from WO 2004/058723), (2.33) 5-fluoro-1,3-dimethyl-N-[4'-(prop-1-yn-1-yl)biphenyl-2-yl]-1H-pyrazole-4-carboxamide (known from WO 2004/058723), (2.34) 2-chloro-N-[4'-(prop-1-yn-1-yl)biphenyl-2-yl]pyridine-3-carboxamide (known from WO 2004/058723), (2.35) 3-(difluoromethyl)-N-[4'-(3,3-dimethylbut-1-yn-1-yl)biphenyl-2-yl]-1-methyl-1H-pyrazole-4-carboxamide (known from WO 2004/058723), (2.36) N-[4'-(3,3-dimethylbut-1-yn-1-yl)biphenyl-2-yl]-5-fluoro-1,3-dimethyl-1H-pyrazole-4-carboxamide (known from WO 2004/058723), (2.37) 3-(difluoromethyl)-N-(4'-ethynylbiphenyl-2-yl)-1-methyl-1H-pyrazole-4-carboxamide (known from WO 2004/058723), (2.38) N-(4'-ethynylbiphenyl-2-yl)-5-fluoro-1,3-dimethyl-1H-pyrazole-4-carboxamide (known from WO 2004/058723), (2.39) 2-chloro-N-(4'-ethynylbiphenyl-2-yl)pyridine-3-carboxamide (known from WO 2004/058723), (2.40) 2-chloro-N-[4'-(3,3-dimethylbut-1-yn-1-yl)biphenyl-2-yl]pyridine-3-carboxamide (known from WO 2004/058723), (2.41) 4-(difluoromethyl)-2-methyl-N-[4'-(trifluoromethyl)biphenyl-2-yl]-1,3-thiazole-5-carboxamide (known from WO 2004/058723), (2.42) 5-fluoro-N-[4'-(3-hydroxy-3-methylbut-1-yn-1-yl)biphenyl-2-yl]-1,3-dimethyl-1H-pyrazole-4-carboxamide (known from WO 2004/058723), (2.43) 2-chloro-N-[4'-(3-hydroxy-3-methylbut-1-yn-1-yl)biphenyl-2-yl]pyridine-3-carboxamide (known from WO 2004/058723), (2.44) 3-(difluoromethyl)-N-[4'-(3-methoxy-3-methylbut-1-yn-1-yl)biphenyl-2-yl]-1-methyl-1H-pyrazole-4-carboxamide (known from WO 2004/058723), (2.45) 5-fluoro-N-[4'-(3-methoxy-3-methylbut-1-yn-1-yl)biphenyl-2-yl]-1,3-dimethyl-1H-pyrazole-4-carboxamide (known from WO 2004/058723), (2.46) 2-chloro-N-[4'-(3-methoxy-3-methylbut-1-yn-1-yl)biphenyl-2-yl]pyridine-3-carboxamide (known from WO 2004/058723) and salts thereof, (15.81) (5-bromo-2-methoxy-4-methylpyridin-3-yl)(2,3,4-trimethoxy-6-methylphenyl)methanone (known from EP-A 1 559 320) and (9.10) N-[2-(4-{[3-(4-chlorophenyl)prop-2-yn-1-yl]oxy}-3-methoxyphenyl)ethyl]-N2-(methylsulfonyl)valinamide (220706-93-4).

The composition according to the invention comprising a mixture of a compound of formula (I) with a bactericide compound can also be particularly advantageous. Examples of suitable bactericide mixing partners can be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The compounds of formula (I) and the fungicide composition according to the invention can be used to curatively or preventively control the phytopathogenic fungi of plants or crops.

Thus, according to a further aspect of the invention, there is provided a method for curatively or preventively controlling the phytopathogenic fungi of plants or crops characterised in that a compound of formula (I) or a fungicide composition according to the invention is applied to the seed, the plant or to the fruit of the plant or to the soil wherein the plant is growing or wherein it is desired to grow.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant.

Among the plants that may be protected by the method according to the invention, mention may be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rye, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots), *Elaeis* sp. (for instance oil palm); horticultural and forest crops; as well as genetically modified homologues of these crops.

Among the diseases of plants or crops that can be controlled by the method according to the invention, mention can be made of:

Powdery Mildew Diseases Such as
*Blumeria* diseases caused for example by *Blumeria graminis;*
*Podosphaera* diseases caused for example by *Podosphaera leucotricha;*
*Sphaerotheca* diseases caused for example by *Sphaerotheca fuliginea;*
*Uncinula* diseases caused for example by *Uncinula necator;*

Rust Diseases Such as
*Gymnosporangium* diseases caused for example by *Gymnosporangium sabinae;*
*Hemileia* diseases caused for example by *Hemileia vastatrix;*
*Phakopsora* diseases caused for example by *Phakopsora pachyrhizi* and *Phakopsora meibomiae;*
*Puccinia* diseases caused for example by *Puccinia recondita, Puccinia graminis* or *Puccinia striiformis;*
*Uromyces* diseases caused for example by *Uromyces appendiculatus;*

Oomycete Diseases Such as
*Albugo* diseases caused for example by *Albugo candida;*
*Bremia* diseases caused for example by *Bremia lactucae;*
*Peronospora* diseases caused for example by *Peronospora pisi* and *Peronospora brassicae;*
*Phytophthora* diseases caused for example by *Phytophthora infestans;*
*Plasmopara* diseases caused for example by *Plasmopara viticola;*
*Pseudoperonospora* diseases caused for example by *Pseudoperonospora humuli* and *Pseudoperonospora cubensis;*
*Pythium* diseases caused for example by *Pythium ultimum;*

Leaf Spot, Leaf Blotch and Leaf Blight Diseases Such as
*Alternaria* diseases caused for example by *Alternaria solani;*
*Cercospora* diseases caused for example by *Cercospora beticola;*
*Cladiosporium* diseases caused for example by *Cladiosporium cucumerinum;*
*Cochliobolus* diseases caused for example by *Cochliobolus sativus* (Conidiaform: *Drechslera*, Syn: *Helminthosporium*) or *Cochliobolus miyabeanus;*
*Colletotrichum* diseases caused for example by *Colletotrichum lindemuthianum;*
*Cycloconium* diseases caused for example by *Cycloconium oleaginum;*
*Diaporthe* diseases caused for example by *Diaporthe citri;*
*Elsinoe* diseases caused for example by *Elsinoe fawcettii;*
*Gloeosporium* diseases caused for example by *Gloeosporium laeticolor;*
*Glomerella* diseases caused for example by *Glomerella cingulata;*
*Guignardia* diseases caused for example by *Guignardia bidwellii;*
*Leptosphaeria* diseases caused for example by *Leptosphaeria maculans* and *Leptosphaeria nodorum;*
*Magnaporthe* diseases caused for example by *Magnaporthe grisea;*
*Mycosphaerella* diseases caused for example by *Mycosphaerella graminicola, Mycosphaerella arachidicola* and *Mycosphaerella fijiensis;*
*Phaeosphaeria* diseases caused for example by *Phaeosphaeria nodorum;*
*Pyrenophora* diseases caused for example by *Pyrenophora teres* or *Pyrenophora tritici repentis;*
*Ramularia*-diseases caused for example by *Ramularia collo-cygni* or *Ramularia areola;*
*Rhynchosporium* diseases caused for example by *Rhynchosporium secalis;*
*Septoria* diseases caused for example by *Septoria apii* and *Septoria lycopersici;*

*Typhula* diseases caused for example by *Thyphula incarnata*;
*Venturia* diseases caused for example by *Venturia inaequalis*;
Root-, Sheath and Stem Diseases Such as
*Corticium* diseases caused for example by *Corticium graminearum*;
*Fusarium* diseases caused for example by *Fusarium oxysporum*;
*Gaeumannomyces* diseases caused for example by *Gaeumannomyces graminis*;
*Rhizoctonia* diseases caused for example by *Rhizoctonia solani*;
*Sarocladium* diseases caused for example by *Sarocladium oryzae*;
*Sclerotium* diseases caused for example by *Sclerotium oryzae*;
*Tapesia* diseases caused for example by *Tapesia acuformis*;
*Thielaviopsis* diseases caused for example by *Thielaviopsis basicola*;
Ear and Panicle Diseases Including Maize Cob Such as
*Alternaria* diseases caused for example by *Alternaria* spp.;
*Aspergillus* diseases caused for example by *Aspergillus flavus*;
*Cladosporium* diseases caused for example by *Cladiosporium cladosporioides*;
*Claviceps* diseases caused for example by *Claviceps purpurea*;
*Fusarium* diseases caused for example by *Fusarium culmorum*;
*Gibberella* diseases caused for example by *Gibberella zeae*;
*Monographella* diseases caused for example by *Monographella nivalis*;
Smut- and Bunt Diseases Such as
*Sphacelotheca* diseases caused for example by *Sphacelotheca reiliana*;
*Tilletia* diseases caused for example by *Tilletia caries*;
*Urocystis* diseases caused for example by *Urocystis occulta*;
*Ustilago* diseases caused for example by *Ustilago nuda*;
Fruit Rot and Mould Diseases Such as
*Aspergillus* diseases caused for example by *Aspergillus flavus*;
*Botrytis* diseases caused for example by *Botrytis cinerea*;
*Penicillium* diseases caused for example by *Penicillium expansum* and *Penicillium purpurogenum*;
*Rhizopus* diseases caused by example by *Rhizopus stolonifer*
*Sclerotinia* diseases caused for example by *Sclerotinia sclerotiorum*;
*Verticillium* diseases caused for example by *Verticillium alboatrum*;
Seed- and Soilborne Decay, Mould, Wilt, Rot and Damping-Off Diseases
*Alternaria* diseases caused for example by *Alternaria brassicicola*;
*Aphanomyces* diseases caused for example by *Aphanomyces euteiches*;
*Ascochyta* diseases caused for example by *Ascochyta lentis*;
*Aspergillus* diseases caused for example by *Aspergillus flavus*;
*Cladosporium* diseases caused for example by *Cladosporium herbarum*;
*Cochliobolus* diseases caused for example by *Cochliobolus sativus*; (Conidiaform: *Drechslera, Bipolaris* Syn: *Helminthosporium*);
*Colletotrichum* diseases caused for example by *Colletotrichum coccodes*;
*Fusarium* diseases caused for example by *Fusarium culmorum*;
*Gibberella* diseases caused for example by *Gibberella zeae*;
*Macrophomina* diseases caused for example by *Macrophomina phaseolina*;
*Microdochium* diseases caused for example by *Microdochium nivale*;
*Monographella* diseases caused for example by *Monographella nivalis*;
*Penicillium* diseases caused for example by *Penicillium expansum*;
*Phoma* diseases caused for example by *Phoma lingam*;
*Phomopsis* diseases caused for example by *Phomopsis sojae*;
*Phytophthora* diseases caused for example by *Phytophthora cactorum*;
*Pyrenophora* diseases caused for example by *Pyrenophora graminea*;
*Pyricularia* diseases caused for example by *Pyricularia oryzae*;
*Pythium* diseases caused for example by *Pythium ultimum*;
*Rhizoctonia* diseases caused for example by *Rhizoctonia solani*;
*Rhizopus* diseases caused for example by *Rhizopus oryzae*;
*Sclerotium* diseases caused for example by *Sclerotium rolfsii*;
*Septoria* diseases caused for example by *Septoria nodorum*;
*Typhula* diseases caused for example by *Typhula incarnata*;
*Verticillium* diseases caused for example by *Verticillium dahliae*;
Canker, Broom and Dieback Diseases Such as
*Nectria* diseases caused for example by *Nectria galligena*;
Blight Diseases Such as
*Monilinia* diseases caused for example by *Monilinia laxa*;
Leaf Blister or Leaf Curl Diseases Including Deformation of Blooms and Fruit Such as
*Exobasidium* diseases caused for example by *Exobasidium vexans*.
*Taphrina* diseases caused for example by *Taphrina deformans*;
Decline Diseases of Wooden Plants Such as
*Esca* disease caused for example by *Phaeomoniella clamydospora, Phaeoacremonium aleophilum* and *Fomitiporia mediterranea*;
*Ganoderma* diseases caused by example by *Ganoderma boninense*;
Diseases of Flowers and Seeds Such as
*Botrytis* diseases caused for example by *Botrytis cinerea*;
Diseases of Tubers Such as
*Rhizoctonia* diseases caused for example by *Rhizoctonia solani*;
*Helminthosporium* diseases caused for example by *Helminthosporium solani*;
Club Root Diseases Such as
*Plasmodiophora* diseases, caused for example by *Plamodiophora brassicae*;

Diseases Caused by Bacterial Organisms Such as
*Xanthomanas* species for example *Xanthomonas campestris* pv. *oryzae;*
*Pseudomonas* species for example *Pseudomonas syringae* pv. *lachrymans;*
*Erwinia* species for example *Erwinia amylovora.*

The fungicide composition according to the invention can also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention; this includes for example direct application, spraying, dipping, injection or any other suitable means.

The dose of active compound usually applied in the methods of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

Furthermore combinations and compositions according to the invention may also be used to reduce the contents of mycotoxins in plants and the harvested plant material and therefore in foods and animal feed stuff made therefrom.

Especially but not exclusively the following mycotoxins can be specified:

Deoxynivalenole (DON), Nivalenole, 15-Ac-DON, 3-Ac-DON, T2-und HT2-Toxins, Fumonisines, Zearalenone Moniliformine, Fusarine, Diaceotoxyscirpenole (DAS), Beauvericine, Enniatine, Fusaroproliferine, Fusarenole, Ochratoxines, Patuline, Ergotalkaloides und Aflatoxines, which are caused for example by the following fungal diseases: *Fusarium* spec., like *Fusarium acuminatum, F. avenaceum, F. crookwellense, F. culmorum, F. graminearum (Gibberella zeae), F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* and others but also by *Aspergillus* spec., *Penicillium* spec., *Claviceps purpurea, Stachybotrys* spec. and others.

The present invention therefore relates to the use of compounds of formula (I) as herein-described for the reduction of mycotoxins in plants and part of plants, and to methods of combating phytopathogenic and mycotoxin producing fungi characterized in that compounds of formula (I) as herein-described are applied to these fungi and/or their habitat.

The present invention therefore relates to the use of compounds of formula (I) as herein-described as insecticide, and/or nematicide.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, co suppression technology or RNA interference—RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted phytopathogenic fungi and/or microorganisms and/or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO-1992/005251, WO-1995/009910, WO-1998/27806, WO-2005/002324, WO-2006/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO-1989/10396 in which, for example, a ribonuclease such as barnase is selectively expressed in the tapetum cells in the stamens. Fertility can then be restored by expression in the tapetum cells of a ribonuclease inhibitor such as barstar (e.g. WO-1991/002069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a *Petunia* EPSPS (Shah et al., Science (1986), 233, 478-481), a Tomato EPSPS (Gasser et al., J. Biol. Chem. (1988),263, 4280-4289), or an *Eleusine* EPSPS (WO-2001/66704). It can also be a mutated EPSPS as described in for example EP-A 0837944, WO-2000/066746, WO-2000/066747 or WO-2002/026995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO-2002/036782, WO-2003/092360, WO-2005/012515 and WO-2007/024782. Glyphosate-tolerant plants can also be obtained by selecting plants containing naturally-occurring mutations of the above-mentioned genes, as described in for example WO-2001/024615 or WO-2003/013226. Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme as described in WO-1996/038567, WO-1999/024585 and WO-1999/024586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO-1999/034008 and WO-2002/36787. Tolerance of plants to HPPD inhibitors can also be improved by transforming plants with a gene encoding an enzyme prephenate dehydrogenase in addition to a gene encoding an HPPD-tolerant enzyme, as described in WO-2004/024928.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyloxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright, Weed Science (2002), 50, 700-712, but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO-1996/033270. Other imidazolinone-tolerant plants are also described in for example WO-2004/040012, WO-2004/106529, WO-2005/020673, WO-2005/093093, WO-2006/007373, WO-2006/015376, WO-2006/024351, and WO-2006/060634. Further sulfonylurea- and imidazolinone-tolerant plants are also described in for example WO-2007/024782.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO-1997/41218, for sugar beet in U.S. Pat. No. 5,773,702 and WO-1999/057965, for lettuce in U.S. Pat. No. 5,198,599, or for sunflower in WO-2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance. An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al., Nat. Biotechnol. (2001), 19, 668-72; Schnepf et al., Applied Environm. Microbiol. (2006), 71, 1765-1774); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034 (WO-2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO-1994/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of poly(ADP-ribose) polymerase (PARP) gene in the plant cells or plants as described in WO-2000/004173 or WO2006/045633 or PCT/EP07/004142.

b. plants which contain a stress tolerance enhancing transgene capable of reducing the expression and/or the activity of the PARG encoding genes of the plants or plants cells, as described e.g. in WO-2004/090140.

c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase as described e.g. in WO2006/032469 or WO-2006/133827 or PCT/EP07/002433.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO-1995/004826, EP 0719338, WO-1996/15248, WO-1996/19581, WO-1996/27674, WO-1997/11188, WO-1997/26362, WO-1997/32985, WO-1997/42328, WO-1997/44472, WO-1997/45545, WO-1998/27212, WO-1998/40503, WO99/58688, WO-1999/58690, WO-1999/58654, WO-2000/008184, WO-2000/008185, WO-2000/008175, WO-2000/28052, WO-2000/77229, WO-2001/12782, WO-2001/12826, WO-2002/101059, WO-2003/071860, WO-2004/056999, WO-2005/030942, WO-2005/030941, WO-2005/095632, WO-2005/095617, WO-2005/095619, WO-2005/095618, WO-2005/123927, WO-2006/018319, WO-2006/103107, WO-2006/108702, WO-2007/009823, WO-2000/22140, WO-2006/063862, WO-2006/072603, WO-2002/034923, EP 06090134.5, EP 06090228.5, EP 06090227.7, EP 07090007.1, EP 07090009.7, WO-2001/14569, WO-2002/79410, WO-2003/33540, WO-2004/078983, WO-2001/19975, WO-1995/26407, WO-1996/34968, WO-1998/20145, WO-1999/12950, WO-1999/66050, WO-1999/53072, U.S. Pat. No. 6,734,341, WO-2000/11192, WO-1998/22604, WO-1998/32326, WO-2001/98509, WO-2001/98509, WO-2005/002359, U.S. Pat. Nos. 5,824,790, 6,013,861, WO-1994/004693, WO-1994/009144, WO-1994/11520, WO-1995/35026, WO-1997/20936.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO-1996/001904, WO-1996/021023, WO-1998/039460, and WO-1999/024593, plants producing alpha 1,4 glucans as disclosed in WO-1995/031553, US 2002/031826, U.S. Pat. Nos. 6,284,479, 5,712,107, WO-1997/047806, WO-1997/047807, WO-1997/047808 and WO-2000/014249, plants producing alpha-1,6 branched alpha-1,4-glucans, as disclosed in WO-2000/73422, plants producing alternan, as disclosed in WO-2000/047727, EP 06077301.7, U.S. Pat. No. 5,908,975 and EP 0728213, 3) transgenic plants which produce hyaluronan, as for example disclosed in WO-2006/032538, WO-2007/039314, WO-2007/039315, WO-2007/039316, JP 2006/304779, and WO-2005/012529.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO-1998/000549 b) Plants, such as cotton plants, containing an altered form of rsw2 or rsw3 homologous nucleic acids as described in WO2004/053219 c) Plants, such as cotton plants, with increased expression of sucrose phosphate synthase as described in WO-2001/017333 d) Plants, such as cotton plants, with increased expression of sucrose synthase as described in WO02/45485 e) Plants, such as cotton plants, wherein the timing of the plasmodesmatal gating at the basis of the fiber cell is altered, e.g. through downregulation of fiberselective β 1,3-glucanase as described in WO2005/017157 f) Plants, such as cotton plants, having fibers with altered reactivity, e.g. through the expression of N-acteylglucosaminetransferase gene including nodC and chitinsynthase genes as described in WO2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants contain a mutation imparting such altered oil characteristics and include:

a) Plants, such as oilseed rape plants, producing oil having a high oleic acid content as described e.g. in U.S. Pat. Nos. 5,969,169, 5,840,946 or 6,323,392 or 6,063,947 b) Plants such as oilseed rape plants, producing oil having a low linolenic acid content as described in U.S. Pat. Nos. 6,270,828, 6,169,190 or 5,965,755 c) Plant such as oilseed rape plants, producing oil having a low level of saturated fatty acids as described e.g. in U.S. Pat. No. 5,434,283

Particularly useful transgenic plants which may be treated according to the invention are plants which comprise one or more genes which encode one or more toxins, such as the following which are sold under the trade names YIELD GARD® (for example maize, cotton, soya beans), Knock-Out® (for example maize), BiteGard® (for example maize), Bt-Xtra® (for example maize), StarLink® (for example maize), Bollgard® (cotton), Nucotn® (cotton), Nucotn 33B®(cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or combination of transformation events, that are listed for example in the databases from various national or regional regulatory agencies (see for example http://gmoinfo.jrc.it/gmp_browse.aspx and http://www.agbios.com/dbase.php).

The compounds or mixtures according to the invention can also be used for the preparation of composition useful to curatively or preventively treat human or animal fungal diseases such as, for example, mycoses, dermatoses, trichophyton diseases and candidiases or diseases caused by *Aspergillus* spp., for example *Aspergillus fumigatus*.

The various aspects of the invention will now be illustrated with reference to the following table of compound examples and the following preparation or efficacy examples.

Table 1 illustrates in a non-limiting manner examples of compounds of formula (I) according to the invention.

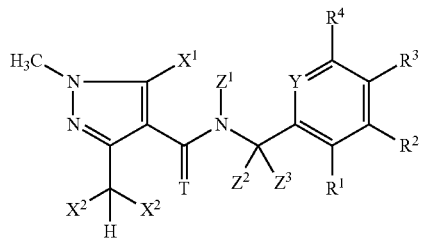

(I)

In table 1, M+H (Apcl+) means the molecular ion peak plus 1 a.m.u. (atomic mass unit) as observed in mass spectroscopy via positive atmospheric pressure chemical ionisation.

In table 1, the log P values were determined in accordance with EEC Directive 79/831 Annex V.A8 by HPLC (High Performance Liquid Chromatography) on a reversed-phase column (C 18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known log P values (determination of the log P values by the retention times using linear interpolation between two successive alkanones). lambda-max-values were determined using UV-spectra from 200 nm to 400 nm and the peak values of the chromatographic signals.

Table 2 provides the NMR data ($^1$H and/or $^{13}$C) of a selected number of compounds from table 1.

| Example | $X^1$ | $X^2$ | T | $Z^1$ | $Z^2$ | $Z^3$ | $R^1$ | $R^2$ | $R^3$ | $R^4$ | Y | $R^5$ | logP | Mass M + H | NMR |
|---|---|---|---|---|---|---|---|---|---|---|---|---|---|---|---|
| 1 | F | F | O | cyclopropyl | H | H | $CF_3$ | H | H | Cl | $CR^5$ | H | 3.8 | 426 | table 2 |
| 2 | F | F | O | cyclopropyl | H | H | $CF_3$ | H | H | H | $CR^5$ | Cl | 3.46 | 426 | table 2 |
| 3 | F | F | O | cyclopropyl | H | H | trimethylsilyl | H | H | H | $CR^5$ | H | 4.36 | 396 | table 2 |
| 4 | F | F | O | cyclopropyl | H | H | Br | H | H | Cl | $CR^5$ | H | 3.67 | 436 | table 2 |
| 5 | F | F | O | cyclopropyl | H | H | $CF_3$ | H | H | Cl | $CR^5$ | F | 3.62 | 444 | table 2 |
| 6 | F | F | O | cyclopropyl | H | H | propan-2-yl | H | H | H | $CR^5$ | H | 3.35 | 366 | table 2 |
| 7 | F | F | S | cyclopropyl | H | H | Cl | H | $CF_3$ | H | N | | 4.11 | 443 | |
| 8 | F | F | O | cyclopropyl | H | H | I | H | H | H | $CR^5$ | F | 3.26 | 468 | |
| 9 | F | F | O | cyclopropyl | H | H | I | H | H | H | $CR^5$ | H | 3.37 | 450 | table 2 |
| 10 | F | F | O | cyclopropyl | H | H | Br | H | H | F | $CR^5$ | F | 3.21 | 438 | |
| 11 | F | F | O | cyclopropyl | H | H | trimethylsilyl | H | H | H | $CR^5$ | F | 4.31 | 414 | table 2 |
| 12 | F | F | O | cyclopropyl | H | H | $CF_3$ | H | H | $CH_3$ | $CR^5$ | H | 3.78 | 406 | |
| 13 | F | F | O | cyclopropyl | H | H | ethyl(dimethyl)silyl | H | H | H | $CR^5$ | H | 4.75 | 410 | |
| 14 | F | F | O | cyclopropyl | H | H | triethylsilyl | H | H | H | $CR^5$ | H | 5.53 | 438 | table 2 |
| 15 | F | F | O | cyclopropyl | H | H | $CF_3$ | H | H | Cl | $CR^5$ | Cl | 3.89 | 460 | |
| 16 | F | F | O | cyclopropyl | H | H | Br | H | Br | F | $CR^5$ | H | 3.96 | 498 | |
| 17 | F | F | O | cyclopropyl | H | H | Br | H | $CH_3$ | Br | $CR^5$ | H | 4.19 | 494 | |
| 18 | F | F | O | cyclopropyl | H | H | Cl | Cl | H | Cl | $CR^5$ | H | 4.11 | 426 | |
| 19 | F | F | O | cyclopropyl | H | H | I | H | H | H | $CR^5$ | Cl | 3.58 | 484 | |
| 20 | F | F | O | cyclopropyl | H | H | I | H | Cl | H | $CR^5$ | H | 3.99 | 484 | |
| 21 | F | F | O | cyclopropyl | H | H | I | H | H | Br | $CR^5$ | H | 3.94 | 528 | |
| 22 | F | F | O | cyclopropyl | H | $CH_3$ | I | H | H | H | $CR^5$ | H | 3.48 | 464 | |
| 22a | F | F | O | cyclopropyl | H | $CH_3$ | I | H | H | H | $CR^5$ | H | | Enantiomer (−) | |
| 22b | F | F | O | cyclopropyl | H | $CH_3$ | I | H | H | H | $CR^5$ | H | | Enantiomer (+) | |
| 23 | F | F | O | cyclopropyl | H | H | I | H | H | Cl | $CR^5$ | H | 3.83 | 484 | |
| 24 | F | F | O | cyclopropyl | H | H | trimethylsilyl | H | H | Cl | $CR^5$ | H | 4.81 | 430 | table 2 |
| 25 | F | F | O | cyclopropyl | H | H | $CF_3$ | H | Cl | Cl | $CR^5$ | H | 4.34 | | |
| 26 | F | F | O | cyclopropyl | H | $CH_3$ | pentyl | H | H | H | $CR^5$ | H | 4.92 | 408 | |
| 27 | F | F | O | cyclopropyl | H | H | pentyl | H | H | H | $CR^5$ | Cl | 5 | 428 | table 2 |
| 28 | F | F | O | cyclopropyl | H | H | pentyl | H | H | H | $CR^5$ | H | 4.62 | 394 | |
| 29 | F | F | O | cyclopropyl | H | H | propan-2-yl | H | H | Cl | $CR^5$ | H | 4.09 | 400 | table 2 |
| 30 | F | F | O | cyclopropyl | H | H | (trifluoromethyl)-sulfanyl | H | H | H | $CR^5$ | H | 3.74 | 424 | |
| 31 | F | F | O | cyclopropyl | H | H | 2-methylpropyl | H | Cl | H | $CR^5$ | H | 4.59 | 414 | |
| 32 | F | F | O | cyclopropyl | H | H | 2-methylpropyl | H | H | H | $CR^5$ | Cl | 4.44 | 414 | table 2 |
| 33 | F | F | O | cyclopropyl | H | H | 2-methylpropyl | H | H | H | $CR^5$ | H | 4.15 | 380 | table 2 |
| 34 | Cl | F | O | cyclopropyl | H | H | propan-2-yl | H | H | H | $CR^5$ | H | 3.81 | 382 | table 2 |
| 35 | Cl | F | O | cyclopropyl | H | H | I | H | H | H | $CR^5$ | H | 3.6 | 466 | table 2 |
| 36 | Cl | F | O | cyclopropyl | H | H | $CF_3$ | H | H | Cl | $CR^5$ | H | 4.01 | 442 | table 2 |
| 37 | Cl | F | O | cyclopropyl | H | H | trimethylsilyl | H | H | H | $CR^5$ | H | 4.49 | 412 | table 2 |
| 38 | F | F | S | cyclopropyl | H | H | trimethylsilyl | H | H | H | $CR^5$ | H | 4.94 | 412 | table 2 |
| 39 | F | F | S | cyclopropyl | H | H | H | H | H | H | $CR^5$ | H | 3.44 | 340 | table 2 |
| 40 | F | F | O | cyclopropyl | H | $CH_3$ | H | Cl | H | Cl | $CR^5$ | H | 4.04 | 406 | table 2 |
| 40a | F | F | O | cyclopropyl | H | $CH_3$ | H | Cl | H | Cl | $CR^5$ | H | | Enantiomer (−) | |
| 40b | F | F | O | cyclopropyl | H | $CH_3$ | H | Cl | H | Cl | $CR^5$ | H | | Enantiomer (+) | |
| 41 | F | F | O | cyclopropyl | H | H | cyclopropyl | H | H | Cl | $CR^5$ | H | 3.87 | 398 | table 2 |
| 42 | F | F | O | cyclopropyl | H | | —$CH_2CH_2CH_2$— | H | propan-2-yloxy | H | $CR^5$ | H | 4.11 | 422 | |
| 43 | F | F | O | cyclopropyl | H | H | $CF_3$ | H | H | I | $CR^5$ | H | 4.01 | 518 | |
| 44 | F | F | O | cyclopropyl | H | $CH_3$ | —$CH_2CH_2C(CH_3)_2CH_2$— | H | H | $CR^5$ | H | 4.89 | 420 | |

-continued

| Example | X¹ | X² | T | Z¹ | Z² | Z³ | R¹ | R² | R³ | R⁴ | Y | R⁵ | logP | Mass M + H | NMR |
|---|---|---|---|---|---|---|---|---|---|---|---|---|---|---|---|
| 44a | F | F | O | cyclopropyl | H | CH₃ | —CH₂CH₂C(CH₃)₂CH₂— | H | H | CR⁵ | H | | Enantiomer (−) $\alpha_D = -0.026$ | | |
| 44b | F | F | O | cyclopropyl | H | CH₃ | —CH₂CH₂C(CH₃)₂CH₂— | H | H | CR⁵ | H | | Enantiomer (+) $\alpha_D = +0.020$ | | |
| 45 | F | F | O | cyclopropyl | H | H | I | H | H | Br | CR⁵ | F | 3.8 | 546 | |
| 46 | F | F | O | cyclopropyl | H | CH₃ | H | CH₃ | H | CH₃ | CR⁵ | H | 3.8 | 366 | table 2 |
| 46a | F | F | O | cyclopropyl | H | CH₃ | H | CH₃ | H | CH₃ | CR⁵ | H | Enantiomer (−) | | |
| 46b | F | F | O | cyclopropyl | H | CH₃ | H | CH₃ | H | CH₃ | CR⁵ | H | Enantiomer (+) | | |
| 47 | F | F | O | cyclopropyl | H | H | cyclopropyl | H | H | H | CR⁵ | H | 3.44 | 364 | |
| 48 | F | F | O | cyclopropyl | H | H | ethyl | H | H | H | CR⁵ | H | 3.33 | 352 | |
| 49 | F | F | O | cyclopropyl | H | H | trimethylsilyl | H | H | F | CR⁵ | F | 4.36 | 432 | |
| 50 | F | F | O | cyclopropyl | H | CH₃ | —CH₂CH(CH₃)CH₂CH₂— | H | H | CR⁵ | H | 4.59 | 406 | | |
| 51 | F | F | O | cyclopropyl | H | CH₃ | —CH₂CH₂CH₂CH₂— | H | H | CR⁵ | H | 4.14 | 392 | | |
| 52 | F | F | O | cyclopropyl | H | H | CF₃ | H | H | Br | CR⁵ | CF₃ | 3.85 | 470 | table 2 |
| 53 | F | F | O | cyclopropyl | H | H | ethyl | H | CH₃ | CH₃ | CR⁵ | H | 4.04 | 380 | |
| 54 | F | F | O | cyclopropyl | H | H | cyclopropyl | H | H | F | CR⁵ | F | 3.51 | 400 | |
| 55 | Cl | F | O | cyclopropyl | H | CH₃ | CF₃ | H | H | H | CR⁵ | H | 3.64 | 422 | |
| 56 | Cl | F | O | cyclopropyl | H | H | CF₃ | H | H | H | CR⁵ | H | 3.58 | 408 | |
| 57 | Cl | F | O | cyclopropyl | H | H | Cl | H | CF₃ | H | N | | 3.55 | 443 | table 2 |
| 58 | Cl | F | O | cyclopropyl | H | CH₃ | Cl | H | Cl | H | N | | 3.69 | 423 | |
| 59 | Cl | F | O | cyclopropyl | H | H | Cl | H | Cl | H | CR⁵ | H | 3.89 | 408 | |
| 60 | Cl | F | O | cyclopropyl | H | CH₃ | H | H | phenoxy | H | CR⁵ | H | 4.31 | 446 | table 2 |
| 61 | F | F | O | cyclopropyl | H | H | CF₃ | H | H | H | CR⁵ | H | 3.39 | 392 | |
| 62 | F | F | O | cyclopropyl | H | CH₃ | Cl | H | Cl | H | N | | 3.48 | 407 | |
| 63 | F | F | O | cyclopropyl | H | H | Cl | H | Cl | H | CR⁵ | H | 3.69 | 392 | |
| 64 | F | F | O | cyclopropyl | H | H | H | phenyl | H | H | CR⁵ | H | 3.78 | 400 | |
| 65 | F | F | O | cyclopropyl | H | CH₃ | H | H | phenoxy | H | CR⁵ | H | 4.14 | 430 | |
| 66 | F | F | O | cyclopropyl | H | CH₃ | CF₃ | H | H | H | CR⁵ | H | 3.42 | 406 | |
| 67 | Cl | F | O | cyclopropyl | H | H | H | phenyl | H | H | CR⁵ | H | 3.94 | 416 | |
| 68 | F | F | O | cyclopropyl | H | H | CF₃ | H | H | F | CR⁵ | F | 3.31 | 428 | |
| 69 | F | F | O | cyclopropyl | H | ethyl | Cl | H | Cl | H | CR⁵ | H | 4.2 | 420 | table 2 |
| 70 | F | F | O | cyclopropyl | H | CH₃ | Cl | H | Cl | H | CR⁵ | H | 3.83 | 406 | table 2 |
| 71 | F | F | O | cyclopropyl | H | ethyl | H | Cl | H | Cl | CR⁵ | H | 4.41 | | |
| 72 | F | F | O | cyclopropyl | H | CH₃ | —OCF₂O— | H | H | CR⁵ | H | 3.58 | 418 | | |
| 73 | F | F | O | cyclopropyl | H | CH₃ | —CH₂C(CH₃)₂— | H | t-Bu | CR⁵ | H | 5.68 | 462 | | |
| 74 | F | F | O | cyclopropyl | H | | —(CH₂)₃— | CH₃ | H | CH₃ | CR⁵ | H | 4.25 | 392 | |
| 75 | F | F | O | cyclopropyl | H | H | Br | H | CH₃ | F | CR⁵ | H | 3.73 | 434 | |
| 76 | F | F | O | cyclopropyl | H | H | terbutyl | H | H | H | CR⁵ | H | 4.06 | 380 | |
| 77 | F | F | O | cyclopropyl | H | CH₃ | H | H | Phenyl-CF₂— | H | CR⁵ | H | 4.23 | 464 | |
| 78 | F | F | O | cyclopropyl | H | CH₃ | H | Phenyl-CF₂— | H | H | CR⁵ | H | 4.15 | 464 | |
| 79 | F | F | O | cyclopropyl | H | H | Cl | H | CH₃ | CH₃ | CR⁵ | H | 3.85 | 386 | |
| 80 | F | F | O | cyclopropyl | H | CH₃ | isopropyl | H | H | H | CR⁵ | H | 3.99 | 380 | table 2 |
| 81 | F | F | O | cyclopropyl | H | CH₃ | ethyl | H | H | H | CR⁵ | H | 3.69 | 366 | table 2 |
| 82 | F | F | O | cyclopropyl | H | H | cyclopentyl | H | H | H | CR⁵ | H | 4.2 | 392 | table 2 |
| 83 | F | F | O | cyclopropyl | H | H | Br | H | H | H | CR⁵ | Cl | 3.42 | 436 | |
| 84 | F | F | O | cyclopropyl | H | H | CF₃ | H | H | H | CR⁵ | F | | 410 | table 2 |
| 85 | F | F | O | cyclopropyl | H | | —CH₂C(CH₃)₂— | H | H | H | CR⁵ | H | 3.87 | 378 | |
| 86 | F | F | O | cyclopropyl | H | | —CH₂CH₂O— | H | H | H | CR⁵ | H | 2.84 | 366 | |
| 87 | F | F | O | cyclopropyl | H | H | Br | —O—CH₂—O— | Br | CR⁵ | H | 3.44 | 524 | | |
| 88 | F | F | O | cyclopropyl | H | H | ethyl | H | H | H | CR⁵ | ethyl | 4.01 | 380 | |
| 89 | F | F | O | cyclopropyl | H | H | Cl | H | CF₃ | H | CR⁵ | Cl | 4.06 | 460 | table 2 |
| 90 | F | F | O | cyclopropyl | H | CH₃ | Cl | H | CF₃ | H | N | | 3.71 | 441 | table 2 |
| 91 | F | F | O | cyclopropyl | H | CH₃ | OCF₃ | H | H | H | CR⁵ | H | 3.6 | 422 | |
| 92 | F | F | O | cyclopropyl | H | H | Br | H | H | H | CR⁵ | Br | 3.51 | 480 | |
| 93 | F | F | O | cyclopropyl | H | butyl | H | H | CF₃ | H | CR⁵ | H | 4.8 | 448 | |
| 94 | F | F | O | cyclopropyl | H | butyl | H | H | H | H | CR⁵ | H | 4.26 | 380 | |
| 95 | F | F | O | cyclopropyl | H | CH₃ | H | H | H | H | CR⁵ | H | 3.06 | 338 | |
| 96 | F | F | O | cyclopropyl | H | CH₃ | Cl | H | H | CF₃ | CR⁵ | H | 3.89 | 440 | |
| 97 | F | F | O | cyclopropyl | H | | —(CH₂)₃— | H | H | H | CR⁵ | Br | 3.78 | 442 | |
| 98 | F | F | O | cyclopropyl | H | CH₃ | Br | H | H | H | CR⁵ | H | 3.31 | 416 | |
| 99 | F | F | O | cyclopropyl | H | | —CH₂CH₂CMe₂— | H | H | H | CR⁵ | H | 4.16 | 392 | |
| 100 | F | F | O | cyclopropyl | H | | —CHBuCH₂— | H | H | H | CR⁵ | H | 4.85 | 406 | |
| 101 | F | F | O | cyclopropyl | H | CH₃ | CF3 | H | H | Cl | CR⁵ | H | 3.92 | 440 | |
| 102 | F | F | O | cyclopropyl | H | | —CH₂CH₂— | CH₃ | H | H | CR⁵ | H | 3.55 | 364 | |
| 103 | F | F | O | cyclopropyl | H | CH₃ | H | I | H | H | CR⁵ | H | 3.76 | 464 | |
| 104 | F | F | O | cyclopropyl | H | H | Cl | CF₃ | H | H | CR⁵ | H | 3.64 | 426 | |
| 105 | F | F | O | cyclopropyl | H | H | OCF₃ | H | H | H | CR⁵ | H | 3.46 | 408 | |
| 106 | F | F | O | cyclopropyl | H | CH₃ | H | Br | H | Br | CR⁵ | H | 4.26 | 494 | |
| 107 | F | F | O | cyclopropyl | H | H | Cl | H | Cl | H | CR⁵ | Cl | 3.99 | 426 | |
| 108 | F | F | O | cyclopropyl | H | H | CH₃ | H | H | H | CR⁵ | CH₃ | 3.31 | 352 | |
| 109 | F | F | O | cyclopropyl | H | | —CH₂CH₂— | H | H | H | CR⁵ | Cl | 3.42 | 384 | |
| 110 | F | F | O | cyclopropyl | H | H | 4-fluoro-phenoxy | H | H | H | CR⁵ | H | 3.85 | 434 | |
| 111 | F | F | O | cyclopropyl | H | H | ethyl | H | H | F | CR⁵ | F | | | table 2 |

-continued

| Example | X¹ | X² | T | Z¹ | Z² | Z³ | R¹ | R² | R³ | R⁴ | Y | R⁵ | logP | Mass M + H | NMR |
|---|---|---|---|---|---|---|---|---|---|---|---|---|---|---|---|
| 112 | F | F | O | cyclopropyl | H | H | 2-methyl-propyl | H | H | F | CR⁵ | F | | | table 2 |
| 113 | F | F | O | cyclopropyl | H | H | cyclopropyl | H | H | H | CR⁵ | Cl | | | table 2 |
| 114 | F | F | O | cyclopropyl | H | H | ethyl | H | H | F | CR⁵ | H | | | table 2 |
| 115 | F | F | O | cyclopropyl | H | H | butyl | H | H | H | CR⁵ | Cl | | | table 2 |
| 116 | F | F | O | cyclopropyl | H | H | trimethylsilyl | H | H | H | CR⁵ | Cl | | | table 2 |
| 117 | F | F | O | cyclopropyl | H | H | CF₃ | H | H | F | CR⁵ | CF3 | | | table 2 |
| 118 | F | F | O | cyclopropyl | H | H | trimethylsilyl | H | H | F | CR⁵ | H | | | table 2 |
| 119 | F | F | O | cyclopropyl | H | H | butyl | H | H | Cl | CR⁵ | H | | | table 2 |
| 120 | F | F | O | cyclopropyl | H | H | 2-methyl-propyl | H | H | Cl | CR⁵ | H | | | table 2 |
| 121 | F | F | O | cyclopropyl | H | H | butyl | H | H | F | CR⁵ | H | | | table 2 |
| 122 | F | F | O | cyclopropyl | H | H | 2-methyl-propyl | H | H | F | CR⁵ | H | | | table 2 |
| 123 | F | F | O | cyclopropyl | H | H | cyclopropyl | H | H | F | CR⁵ | H | | | table 2 |
| 124 | F | F | O | cyclopropyl | H | H | ethyl | H | H | H | CR⁵ | Cl | | | table 2 |
| 125 | F | F | O | cyclopropyl | H | H | ethyl | H | H | Cl | CR⁵ | H | | | table 2 |
| 126 | F | F | O | cyclopropyl | H | H | butyl | H | H | F | CR⁵ | F | | | table 2 |
| 127 | F | F | O | cyclopropyl | H | H | 2-methyl-propyl | H | H | F | CR⁵ | F | | | table 2 |
| 128 | F | F | O | cyclopropyl | H | H | butyl | H | H | F | CR⁵ | F | | | table 2 |
| 129 | F | F | O | cyclopropyl | H | H | ethyl | H | H | H | CR⁵ | F | | | table 2 |
| 130 | F | F | O | cyclopropyl | H | H | cyclopropyl | H | H | H | CR⁵ | F | | | table 2 |
| 131 | F | F | S | cyclopropyl | H | H | propan-2-yl | H | H | H | CR⁵ | H | 4.36 | 382 | table 2 |
| 132 | F | F | S | cyclopropyl | H | H | Cl | H | H | H | CR⁵ | CF₃ | 4.23 | 442 | |
| 133 | F | F | S | cyclopropyl | H | H | ethyl | H | H | H | CR⁵ | H | 4.06 | | |
| 134 | F | F | O | cyclopropyl | H | H | propan-2-yl | H | H | H | CR⁵ | F | | | |
| 135 | F | F | O | cyclopropyl | H | H | propan-2-yl | H | H | F | CR⁵ | H | | | table 2 |
| 136 | F | F | O | cyclopropyl | H | H | propan-2-yl | H | H | F | CR⁵ | F | | | table 2 |
| 137 | F | F | O | cyclopropyl | H | H | cyclopentyl | H | H | H | CR⁵ | F | | | table 2 |
| 138 | F | F | O | cyclopropyl | H | H | cyclopentyl | H | H | F | CR⁵ | H | | | table 2 |
| 139 | F | F | O | cyclopropyl | H | H | cyclopentyl | H | H | F | CR⁵ | F | | | table 2 |
| 140 | F | F | O | cyclopropyl | H | H | cyclopentyl | H | H | Cl | CR⁵ | H | | | table 2 |
| 141 | F | F | O | cyclopropyl | H | H | cyclopentyl | H | H | H | CR⁵ | Cl | | | table 2 |
| 142 | F | F | O | 2-methyl-cyclopropyl | H | H | ethyl | H | H | H | CR⁵ | H | | | table 2 |
| 143 | F | F | O | 2-methyl-cyclopropyl | H | H | trimethylsilyl | H | H | H | CR⁵ | H | | | table 2 |
| 144 | F | F | O | 2-methyl-cyclopropyl | H | H | CF₃ | H | H | H | CR⁵ | Cl | | | table 2 |
| 145 | Cl | F | O | cyclopropyl | H | H | ethyl | H | H | Cl | CR⁵ | H | | | |
| 146 | Cl | F | O | cyclopropyl | H | H | propan-2-yl | H | H | F | CR⁵ | H | 3.92 | 400 | |
| 147 | Cl | F | O | cyclopropyl | H | H | CF₃ | H | H | F | CR⁵ | H | | | |
| 148 | Cl | F | O | cyclopropyl | H | H | butyl | H | H | Cl | CR⁵ | H | | | |
| 149 | Cl | F | O | cyclopropyl | H | H | 2-Methyl-propyl | H | H | Cl | CR⁵ | H | | | |
| 150 | Cl | F | O | cyclopropyl | H | H | 2-Methyl-propyl | H | H | H | CR⁵ | Cl | 4.74 | 430 | |
| 151 | Cl | F | O | cyclopropyl | H | H | trimethylsilyl | H | H | H | CR⁵ | Cl | 4.82 | 446 | |
| 152 | Cl | F | O | cyclopropyl | H | H | cyclopentyl | H | H | Cl | CR⁵ | H | 4.92 | 442 | |
| 153 | Cl | F | O | cyclopropyl | H | H | cyclopropyl | H | H | F | CR⁵ | H | | | |
| 154 | F | F | O | cyclopropyl | H | H | 1,3-dimethyl-butyl | H | H | H | CR⁵ | H | 4.82 | 408 | |
| 155 | F | F | O | cyclopropyl | H | H | 2-cyclopropyl-cyclopropyl | H | H | H | CR⁵ | H | 4.25 | 404 | |
| 156 | F | F | O | cyclopropyl | H | H | butan-2-yl | H | H | H | CR⁵ | H | 4.06 | 380 | |
| 157 | F | F | O | 2-methyl-cyclopropyl | H | H | propan-2-yl | H | H | H | CR⁵ | H | | | table 2 |

TABLE 2

| Example | NMR |
|---|---|
| 1 | ¹³C NMR (400 MHz, DMSO-d6) δ ppm: 8.76, 22.87, 30.58, 34.78, 36.95, 47.27, 107.72, 110.08, 112.44, 127.40, 127.53, 127.59, 127.65, 127.70, 128.24 |
| 2 | ¹³C NMR (400 MHz, DMSO-d6) δ ppm: 9.05, 28.31, 34.71, 44.60, 107.24, 109.61, 111.97, 125.25, 125.31, 125.37, 128.95, 133.99 |
| 3 | ¹H NMR (400 MHz, DMSO-d6) δ ppm: 0.36 (s, 9H), 0.53 (bs, 2H) 0.64 (d, 2H), 2.86 (bs, 1H), 3.82 (bs, 3H), 4.77 (bs, 2H), 7.00 (t, J = 54.06 Hz, 1H), 7.11-7.49 (m, 4H) ¹³C NMR (400 MHz, DMSO-d6) δ ppm: 0.00, 8.62, 30.24, 34.54, 50.84, 109.78, 124.83, 126.08, 129.44, 134.48 |
| 4 | ¹³C NMR (400 MHz, DMSO-d6) δ ppm: 9.07, 34.76, 51.10, 107.61, 109.98, 112.34, 129.02, 129.16, 133.99 |
| 5 | ¹³C NMR (400 MHz, DMSO-d6) δ ppm: 9.08, 28.78, 34.72, 41.48, 107.28, 109.65, 112.01, 122.52, 122.57, 122.62, 130.05 |
| 6 | ¹³C NMR (400 MHz, DMSO-d6) δ ppm: 9.15, 23.73, 28.59, 29.60, 34.72, 47.82, 107.48, 109.85, 112.21, 125.54, 125.71, 127.96, 129.07 |
| 9 | ¹³C NMR (400 MHz, DMSO-d6) δ ppm: 9.04, 34.74, 109.92, 112.28, 128.45, 128.66, 129.10, 139.67 |

TABLE 2-continued

| Example | NMR |
|---|---|
| 11 | $^{13}$C NMR (400 MHz, DMSO-d6) δ ppm: −0.00, 8.51, 34.04, 115.94, 116.17, 128.02, 128.10, 129.86, 129.90 |
| 14 | $^{13}$C NMR (400 MHz, DMSO-d6) δ ppm: 4.17, 4.43, 7.57, 8.73, 34.72, 51.00, 124.80, 126.09, 128.64, 129.46, 135.84 |
| 24 | $^{13}$C NMR (400 MHz, DMSO-d6) δ ppm: 0.00, 8.78, 30.25, 34.70, 50.63, 109.97, 125.22, 126.35, 135.99 |
| 27 | $^{13}$C NMR (400 MHz, DMSO-d6) δ ppm: 9.21, 13.99, 22.58, 28.48, 31.17, 31.67, 33.18, 34.69, 107.33, 109.69, 112.05, 127.58, 128.11, 128.79 |
| 29 | $^{13}$C NMR (400 MHz, DMSO-d6) δ ppm: 8.62, 9.17, 23.62, 28.33, 29.78, 30.32, 34.75, 45.79, 107.52, 109.89, 112.25, 127.10, 127.94, 128.50 |
| 30 | $^{13}$C NMR (400 MHz, DMSO-d6) δ ppm: 8.82, 34.73, 107.64, 110.00, 112.37, 128.33, 128.68, 131.87, 138.63 |
| 32 | $^{13}$C NMR (400 MHz, DMSO-d6) δ ppm: 9.15, 22.36, 28.47, 30.33, 34.70, 42.34, 44.62, 107.34, 109.71, 112.07, 127.73, 128.48, 129.14 |
| 33 | $^{13}$C NMR (400 MHz, DMSO-d6) δ ppm: 8.96, 22.53, 29.70, 34.70, 41.79, 107.55, 109.92, 112.28, 126.12, 127.03, 127.89, 130.50 |
| 34 | $^{13}$C NMR (400 MHz, DMSO-d6) δ ppm: 23.72, 28.59, 36.91, 110.27, 125.33, 125.73, 127.81, 128.74 |
| 35 | $^{13}$C NMR (400 MHz, DMSO-d6) δ ppm: 6.25, 8.79, 30.78, 36.94, 37.17, 55.89, 108.01, 110.37, 112.72, 128.33, 128.49, 129.04, 139.55 |
| 36 | $^{13}$C NMR (400 MHz, DMSO-d6) δ ppm: 5.91, 8.46, 30.89, 36.95, 46.94, 108.16, 110.51, 112.87, 127.31, 127.47, 127.52, 128.26 |
| 37 | $^{13}$C NMR (400 MHz, DMSO-d6) δ ppm: −0.00, 5.57, 8.21, 30.63, 36.68, 50.76, 110.17, 125.13, 125.97, 129.31, 134.32 |
| 38 | $^{1}$H NMR (250 MHz, DMSO-d6) δ ppm: 0.37 (s, 9H), 0.54-0.74 (m, 4H), 3.11 (bs, 1H), 3.83 (s, 3H), 5.41 (bs, 2H), 7.14 (t, J = 54.40 Hz, 1H), 7.04-7.51 (m, 4H) |
| 39 | $^{13}$C NMR (400 MHz, DMSO-d6) δ ppm: 0.01, 10.10, 34.69, 34.99, 35.04, 58.78, 107.56, 109.93, 112.30, 127.24, 127.68, 127.76, 127.99, 128.71, 128.91 |
| 40 | $^{13}$C NMR (400 MHz, DMSO-d6) δ ppm: 7.30, 9.01, 17.02, 27.64, 27.70, 34.70, 34.81, 53.95, 110.16, 112.53, 125.52, 127.40 |
| 41 | $^{13}$C NMR (400 MHz, DMSO-d6) δ ppm: 7.27, 7.34, 9.09, 12.40, 34.76, 127.45, 127.51, 127.83 |
| 42 | $^{13}$C NMR (400 MHz, DMSO-d6) δ ppm: 6.38, 9.65, 21.96, 22.05, 22.15, 22.51, 23.39, 28.15, 29.97, 30.17, 34.67, 38.91, 69.69, 69.97, 107.86, 110.22, 112.58, 113.96, 114.07, 114.19, 115.86, 127.64, 129.67 |
| 44 | $^{13}$C NMR (400 MHz, DMSO-d6) δ ppm: 7.81, 8.71, 18.51, 22.67, 26.36, 27.40, 27.46, 29.20, 34.68, 35.79, 44.18, 52.33, 109.87, 125.14, 125.21, 129.49 |
| 46 | $^{13}$C NMR (400 MHz, DMSO-d6) δ ppm: 7.11, 8.73, 17.30, 21.41, 27.39, 30.31, 34.65, 54.44, 107.77, 110.13, 112.49, 124.70, 128.69 |
| 51 | $^{13}$C NMR (400 MHz, DMSO-d6) δ ppm: 7.88, 8.72, 18.57, 22.83, 23.20, 25.36, 27.48, 27.54, 30.21, 34.67, 52.31, 107.50, 109.86, 112.22, 124.99, 125.22, 129.04 |
| 52 | $^{13}$C NMR (400 MHz, DMSO-d6) δ ppm: 8.75, 30.53, 34.77, 47.19, 107.72, 110.08, 112.45, 127.62, 127.67, 127.73, 127.79, 130.44, 131.21 |
| 57 | $^{13}$C NMR (400 MHz, DMSO-d6) δ ppm: 8.60, 9.03, 31.42, 36.96, 37.06, 45.71, 50.78, 107.59, 109.94, 112.30, 134.02, 143.88 |
| 60 | $^{13}$C NMR (400 MHz, DMSO-d6) δ ppm: 6.94, 8.03, 8.45, 17.15, 27.56, 36.86, 108.19, 110.55, 112.90, 118.54, 118.91, 123.31, 128.48, 129.76 |
| 69 | $^{13}$C NMR (400 MHz, DMSO-d6) δ ppm: 8.17, 9.07, 11.13, 25.05, 28.79, 28.86, 34.62, 34.83, 60.09, 107.53, 108.88, 109.88, 112.24, 126.89, 129.62, 130.55 |
| 70 | $^{13}$C NMR (400 MHz, DMSO-d6) δ ppm: 8.16, 8.75, 18.18, 28.48, 28.55, 34.64, 53.99, 107.45, 109.82, 112.18, 126.88, 129.44, 130.23 |
| 72 | $^{13}$C NMR (400 MHz, DMSO-d6) δ ppm: 4.80, 7.92, 8.91 , 17.35, 28.63, 28.70, 34.66, 52.64, 52.80, 107.55, 108.56, 109.90, 112.26, 122.21, 122.73, 123.45, 124.01 |
| 73 | $^{13}$C NMR (400 MHz, DMSO-d6) δ ppm: 7.92, 8.40, 17.76, 27.38, 27.45, 27.77, 28.45, 28.82, 31.62, 31.65, 31.71, 34.65, 34.82, 41.42, 41.56, 53.62, 107.49, 108.88, 109.86, 112.22 |
| 74 | $^{13}$C NMR (400 MHz, DMSO-d6) δ ppm: 6.42, 9.75, 19.69, 20.89, 21.01, 22.38, 22.73, 26.52, 27.52, 28.24, 34.67, 56.32, 107.94, 110.30, 112.66, 124.34, 129.04 |
| 80 | $^{13}$C NMR (400 MHz, DMSO-d6) δ ppm: 1.03, 8.06, 8.53, 8.84, 18.56, 22.97, 25.17, 27.46, 27.53, 27.89, 34.65, 34.77, 45.72, 51.59, 107.50, 109.87, 112.23, 125.33, 125.58, 127.93, 128.19 |
| 81 | $^{13}$C NMR (400 MHz, DMSO-d6) δ ppm: 8.03, 8.82, 14.76, 18.50, 24.30, 27.42, 27.49, 29.71, 34.64, 52.06, 107.53, 109.88, 112.24, 125.49, 127.84, 127.95, 128.19 |
| 82 | $^{13}$C NMR (400 MHz, DMSO-d6) δ ppm: 6.79, 9.11, 25.72, 25.85, 34.45, 34.56, 34.73, 40.63, 58.46, 109.87, 112.24, 125.63, 126.14, 127.80, 128.64 |
| 84 | $^{1}$H NMR (300 MHz, CHCl3-d) δ ppm: 0.60-0.64 (m, 4H), 2.51 (bs, 1H), 3.79 (s, 3H), 4.97 (s, 2H), 6.91 (t, J = 54.4 Hz, 1H), 7.27-7.33 (m, 1H), 7.39-7.46 (m, 1H), 7.52 (d, 1H). $^{13}$C NMR (400 MHz, DMSO-d6) δ ppm: 8.99, 34.69, 109.64, 119.55, 119.79, 122.28, 129.53, 129.62 |
| 87 | $^{13}$C NMR (400 MHz, DMSO-d6) δ ppm: 9.14, 31.44, 34.75, 36.50, 102.00, 109.92, 125.63 |
| 89 | $^{13}$C NMR (400 MHz, DMSO-d6) δ ppm: 9.24, 34.74, 109.66, 125.55, 125.59 |
| 90 | $^{13}$C NMR (400 MHz, DMSO-d6) δ ppm: 8.63, 9.24, 9.44, 16.76, 27.55, 27.62, 34.69, 45.80, 55.51, 109.68, 134.31, 143.61, 143.65 |
| 111 | $^{1}$H NMR (300 MHz, CHCl3-d): d 0.64 (d, 4H), 1.21 (t, 3H), 2.50 (bs, 1H), 2.64 (q, 2H), 3.79 (s, 3H), 4.81 (s, 2H), 6.87 (t, J = 54.4 Hz, 1H), 6.96-7.09 (m, 2H). |
| 112 | $^{1}$H NMR (300 MHz, CHCl3-d): d 0.64 (d, 4H), 0.90 (d, 6H), 1.79-1.83 (m, 1H), 2.55 (m, 3H), 3.79 (s, 3H), 4.79 (s, 2H), 6.87 (t, J = 54.4 Hz, 1H), 6.89-7.06 (m, 2H). |

TABLE 2-continued

| Example | NMR |
|---|---|
| 113 | $^1$H NMR (300 MHz, CHCl3-d): d 0.56-0.58 (m, 2H), 0.66-0.70 (m, 4H), 0.92-0.99 (m, 2H), 1.98-2.01 (m, 1H), 2.39 (bs, 1H), 3.79 (s, 3H), 5.12 (s, 2H), 6.93 (t, J = 54.4 Hz, 1H), 6.87-7.23 (m, 3H). |
| 114 | $^1$H NMR (300 MHz, CHCl3-d): d 0.65-0.66 (m, 4H), 1.21 (t, 3H), 2.62 (q, 2H), 2.64 (bs, 1H), 3.81 (s, 3H), 4.71 (s, 2H), 6.86 (t, J = 54.6 Hz, 1H), 6.89-6.95 (m, 2H), 7.13-7.18 (m, 1H). |
| 115 | $^1$H NMR (300 MHz, CHCl3-d): d 0.53-0.60 (m, 4H), 0.90 (t, 3H), 1.31-1.38 (m, 2H), 1.48-1.57 (m, 2H), 2.37 (bs, 1H), 2.69-2.74 (m, 2H), 3.79 (s, 3H), 4.90 (s, 2H), 6.93 (t, J = 54.6 Hz, 1H), 7.12-7.21 (m, 3H). |
| 116 | $^1$H NMR (300 MHz, CHCl3-d): d 0.35 (s, 9H), 0.46 (m, 4H), 2.58 (bs, 1H), 3.80 (s, 3H), 4.92 (s, 2H), 6.92 (t, J = 54.7 Hz, 1H), 7.10-7.43 (m, 3H). |
| 117 | $^1$H NMR (300 MHz, CHCl3-d): d 0.62-0.70 (m, 4H), 2.89 (bs, 1H), 3.83 (s, 3H), 4.92 (s, 2H), 6.84 (t, J = 54.6 Hz, 1H), 7.02-7.25 (m, 2H), 7.64-7.69 (m, 1H). |
| 118 | $^1$H NMR (300 MHz, CHCl3-d): d 0.36 (s, 9H), 0.56-0.65 (m, 4H), 2.90 (bs, 1H), 3.83 (s, 3H), 4.86 (s, 2H), 6.68-7.04 (m, 3H), 7.44-7.49 (m, 1H). $^{13}$C NMR (400 MHz, DMSO-d6) δ ppm: −0.00, 8.64, 34.60, 50.68, 109.84, 112.13, 112.34, 112.89, 113.09, 136.43, 136.50 |
| 119 | $^1$H NMR (300 MHz, CHCl3-d): d 0.65-0.68 (m, 4H), 0.92 (t, 3H), 1.33-1.40 (m, 2H), 1.49-1.54 (m, 2H), 2.60 (t, 2H), 2.65 (bs, 1H), 3.81 (s, 3H), 4.71 (s, 2H), 6.85 (t, J = 54.6 Hz, 1H), 7.04-7.20 (m, 3H). |
| 120 | $^1$H NMR (300 MHz, CHCl3-d): d 0.64-0.65 (m, 4H), 0.92 (d, 6H), 1.80-1.84 (m, 1H), 2.50 (d, 2H), 2.74 (bs, 1H), 3.81 (s, 3H), 4.71 (s, 2H), 6.85 (t, J = 54.6 Hz, 1H), 7.05-7.18 (m, 3H). |
| 121 | $^1$H NMR (300 MHz, CHCl3-d): d 0.64-0.66 (m, 4H), 0.92 (t, 3H), 1.33-1.41 (m, 2H), 1.49-1.54 (m, 2H), 2.60 (t, 2H), 2.74 (bs, 1H), 3.81 (s, 3H), 4.71 (s, 2H), 6.86 (t, J = 54.6 Hz, 1H), 6.87-6.92 (m, 2H), 7.04-7.12 (m, 1H). |
| 122 | $^1$H NMR (300 MHz, CHCl3-d): d 0.63-0.67 (m, 4H), 0.93 (d, 6H), 1.79-1.83 (m, 1H), 2.50 (d, 2H), 2.76 (bs, 1H), 3.81 (s, 3H), 4.71 (s, 2H), 6.67-7.07 (m, 4H). |
| 123 | $^1$H NMR (300 MHz, CHCl3-d): d 0.60-0.66 (m, 6H), 0.89-0.95 (m, 2H), 1.82-1.84 (m, 1H), 2.73 (bs, 1H), 3.81 (s, 3H), 4.89 (s, 2H), 6.68-6.99 (m, 4H). |
| 124 | $^1$H NMR (300 MHz, CHCl3-d): d 0.52-0.62 (m, 4H), 1.21 (t, 3H), 2.37 (bs, 1H), 2.75 (q, 2H), 3.79 (s, 3H), 4.93 (s, 2H), 6.93 (t, J = 54.4 Hz, 1H), 7.11-7.20 (m, 3H). |
| 125 | $^1$H NMR (300 MHz, CHCl3-d): d 0.65-0.69 (m, 4H), 1.21 (t, 3H), 2.62-2.64 (m, 3H), 3.81 (s, 3H), 4.70 (s, 2H), 6.85 (t, J = 54.6 Hz, 1H), 7.04-7.22 (m, 3H). |
| 126 | $^1$H NMR (300 MHz, CHCl3-d): d 0.65 (d, 4H), 0.88 (t, 3H), 1.29-1.37 (m, 2H), 1.46-1.54 (m, 2H), 2.51 (bs, 1H), 2.63 (t, 2H), 3.79 (s, 3H), 4.80 (s, 2H), 6.88 (t, J = 54.6 Hz, 1H), 6.90-7.03 (m, 2H). |
| 127 | $^1$H NMR (300 MHz, DMSO-d6): d 0.54-0.57 (m, 4H), 0.82 (d, 6H), 1.73-1.78 (m, 1H), 2.33 (bs, 1H), 2.54 (d, 2H), 3.75 (s, 3H), 4.68 (s, 2H), 6.76-7.12 (m, 3H), 7.23-7.30 (m, 1H). |
| 128 | $^1$H NMR (300 MHz, CHCl3-d): d 0.55-0.62 (m, 4H), 0.89 (t, 3H), 1.25-1.42 (m, 2H), 1.49-1.54 (m, 2H), 2.46 (bs, 1H), 2.67 (t, 2H), 3.78 (s, 3H), 4.79 (s, 2H), 6.89 (t, J = 54.5 Hz, 1H), 6.88-7.07 (m, 2H), 7.17-7.22 (m, 1H). |
| 129 | $^1$H NMR (300 MHz, CHCl3-d): d 0.60-0.64 (m, 4H), 1.20 (t, 3H), 2.50 (bs, 1H), 2.68 (q, 2H), 3.78 (s, 3H), 4.80 (s, 2H), 6.71-7.07 (m, 3H), 7.22-7.23 (m, 1H). |
| 130 | $^1$H NMR (300 MHz, CHCl3-d): d 0.59-0.61 (m, 2H), 0.65-0.70 (m, 4H), 0.91-0.97 (m, 2H), 1.96 (bs, 1H), 2.44 (bs, 1H), 3.79 (s, 3H), 4.96 (s, 2H), 6.89 (t, J = 54.6 Hz, 1H), 6.72-7.23 (m, 3H). |
| 131 | $^{13}$C NMR (400 MHz, DMSO-d6) δ ppm: 10.41, 23.67, 28.95, 34.71, 34.99, 35.04, 56.09, 109.77, 112.14, 125.52, 125.79, 126.07, 128.12, 128.29, 128.46 |
| 135 | $^1$H NMR (300 MHz, CHCl3-d): d 0.65-0.69 (m, 4H), 1.22 (d, 6H), 2.69 (bs, 1H), 3.10-3.14 (m, 1H), 3.81 (s, 3H), 4.75 (s, 2H), 6.86 (t, J = 54.6 Hz, 1H), 6.88-6.93 (m, 2H), 7.23-7.28 (m, 1H). |
| 136 | $^1$H NMR (300 MHz, CHCl3-d): d 0.66 (d, 4H), 1.19 (d, 6H), 2.47 (bs, 1H), 3.12-3.19 (m, 1H), 3.78 (s, 3H), 4.83 (s, 2H), 6.89 (t, J = 54.6 Hz, 1H), 7.03-7.13 (m, 2H). |
| 137 | $^1$H NMR (300 MHz, CHCl3-d): d 0.59-0.62 (m, 4H), 1.56-1.63 (m, 2H), 1.65-1.75 (m, 2H), 1.76-1.82 (m, 2H), 1.95-2.02 (m, 2H), 2.41-2.44 (m, 1H), 3.22-3.27 (m, 1H), 3.79 (s, 3H), 4.84 (s, 2H), 6.89 (t, J = 52.5 Hz, 1H), 6.86-7.26 (m, 3H). |
| 138 | $^1$H NMR (300 MHz, CHCl3-d): d 0.64-0.68 (m, 4H), 1.56-1.62 (m, 2H), 1.62-1.70 (m, 2H), 1.76-1.83 (m, 2H), 1.96-2.05 (m, 2H), 2.71 (bs, 1H), 3.13-3.19 (m, 1H), 3.81 (s, 3H), 4.76 (s, 2H), 6.86 (t, J = 54.6 Hz, 1H), 6.87-6.97 (m, 2H), 7.23-7.28 (m, 1H). |
| 139 | $^1$H NMR (300 MHz, CHCl3-d): d 0.62-0.64 (d, 4H), 1.56-1.61 (m, 2H), 1.62-1.68 (m, 2H), 1.70-1.83 (m, 2H), 1.94-2.04 (m, 2H), 2.47 (bs, 1H), 3.17-3.23 (m, 1H), 3.79 (s, 3H), 4.84 (s, 2H), 6.88 (t, J = 54.6 Hz, 1H), 7.04-7.11 (m, 2H). |
| 140 | $^1$H NMR (300 MHz, CHCl3-d): d 0.65-0.69 (m, 4H), 1.56-1.62 (m, 2H), 1.66-1.73 (m, 2H), 1.78-1.83 (m, 2H), 1.96-2.03 (m, 2H), 2.70 (bs, 1H), 3.14-3.19 (m, 1H), 3.81 (s, 3H), 4.75 (s, 2H), 6.86 (t, J = 54.6 Hz, 1H), 7.18-7.23 (m, 3H). |
| 141 | $^1$H NMR (300 MHz, CHCl3-d): d 0.56-0.58 (m, 4H), 1.56-1.63 (m, 2H), 1.65-1.72 (m, 2H), 1.78-1.81 (m, 2H), 2.00-2.02 (m, 2H), 2.39 (bs, 1H), 3.28-3.33 (m, 1H), 3.79 (s, 3H), 4.98 (s, 2H), 6.93 (t, J = 54.4 Hz, 1H), 7.12-7.26 (m, 3H). |
| 142 | $^1$H NMR (300 MHz, DMSO-d6): δ 0.43 (q, 1H), 0.68 (d, 3H), 0.60-0.80 (m, 1H), 0.90-1.00 (m, 1H), 1.16 (t, 3H), 2.15-2.35 (m, 1H), 2.62 (q, 2H), 3.80 (s, 3H), 4.51 (d, 1H), 4.77 (d, 1H), 6.98 (t, J = 53.8 Hz, 1H), 7.10-7.30 (m, 4H). |
| 143 | $^1$H NMR (300 MHz, DMSO-d6): δ 0.35 (s, 9H), 0.35-0.45 (m, 1H), 0.60-0.70 (m, 4H), 0.80-0.95 (m, 1H), 3.83 (s, 3H), 4.61 (d, 1H), 4.87 (d, 1H), 6.99 (t, J = 53.7 Hz, 1H), 7.10 (d, 1H) 7.25 (t, 1H) 7.38 (t, 1H) 7.49 (d, 1H). |

TABLE 2-continued

| Example | NMR |
|---|---|
| 144 | $^1$H NMR (300 MHz, DMSO-d6): δ 0.31-0.33 (m, 1H), 0.53 (d, 3H), 0.66-0.67 (m, 1H), 0.80 (m, 1H), 2.01 (bs, 1H), 3.77 (s, 3H), 4.83-4.98 (m, 2H), 6.95 (t, J = 53.8 Hz, 1H), 7.59 (t, 1H) 7.79-7.82 (m, 2H). |
| 157 | $^1$H NMR (300 MHz, DMSO-d6): d 0.41-0.43 (m, 1H), 0.65-0.67 (m, 3H), 0.74-0.78 (m, 1H), 0.80-0.86 (m, 1H), 1.14 (m, 6H), 2.14-2.16 (m, 1H), 3.10 (bs, 1H), 3.78 (s, 3H), 4.48-4.81 (m, 2H), 6.96 (t, J = 53.8 Hz, 1H), 7.13-7.20 (m, 4H). |

The following examples illustrate in a non limiting manner the preparation and efficacy of the compounds of formula (I) according to the invention.

Synthesis of 5-chloro-3-(difluoromethyl)-1-methyl-1H-pyrazole-4-carboxylic acid (example IIb-1)

In a 500 ml flask, 6.0 g (31 mmol) of 5-chloro-3-(difluoromethyl)-1-methyl-1H-pyrazole-4-carbaldehyde were added to 30 ml of toluene. A solution of 2.4 g (62 mmol) of sodium hydroxide in 6 ml of water was added to the reaction mixture, followed by 103 ml of a 30% solution of hydrogen peroxide in water, whilst keeping the temperature below 37° C. After the end of the addition, the reaction mixture was stirred at 50° C. for 7 hours. Once the reaction mixture was back to room temperature, the two phases were separated and the organic phase was extracted with 100 ml of water. The combined aqueous phases were acidified to pH 2 with aqueous hydrochloric acid. The resulting white precipitate was filtered, washed with 2*20 ml of water, and dried to yield 3.2 g of 5-chloro-3-(difluoromethyl)-1-methyl-1H-pyrazole-4-carboxylic acid as a white solid.

$^1$H NMR (400 MHz, DMSO-d$_6$) δ ppm: 3.78 (s, 3H); 7.12 (t, 1H, J$_{HF}$=53.60 Hz) 13.19 (s, 1H); IR (KBr): 1688 cm$^{-1}$ (C=O); 2200-3200 cm$^{-1}$ broad (hydrogen bond);

Synthesis of 5-chloro-3-(difluoromethyl)-1-methyl-1H-pyrazole-4-carbonyl chloride (example IIc-1)

3.2 g of 5-chloro-3-(difluoromethyl)-1-methyl-1H-pyrazole-4-carboxylic acid and 44.3 ml of thionyl chloride were refluxed for 5 hours. After cooling down, the reaction mixture was evaporated under vacuum to yield 3.5 g of 5-chloro-3-(difluoromethyl)-1-methyl-1H-pyrazole-4-carbonyl chloride as a yellow oil.

$^1$H NMR (400 MHz, CHCl$_3$-d$_6$) δ ppm: 3.97 (s, 3H); 7.00 (t, J=52.01 Hz, 1 H);
IR (TQ): 1759 and 1725 cm$^{-1}$ (C=O);

Synthesis of 3-(difluoromethyl)-5-fluoro-1-methyl-1H-pyrazole-4-carbonyl fluoride (example IId-1)

To a dried solution of 4.0 g (70 mmol) of potassium fluoride in 21 ml of tetrahydrothiophene-1,1-dioxide was added a solution of 5.0 g (22 mmol) of 5-chloro-3-(difluoromethyl)-1-methyl-1H-pyrazole-4-carbonyl chloride in 15 ml of toluene at 100° C. The resulting reaction mixture was stirred at 190-200° C. for 22 hours. Distillation under vacuum yielded 8 g of a solution (25% molar) of 3-(difluoromethyl)-5-fluoro-1-methyl-1H-pyrazole-4-carbonyl fluoride in tetrahydro-thiophene-1,1-dioxide.

$^1$H NMR (250 MHz, CHCl$_3$-d$_6$) δ ppm: 3.87 (s, 3H); 6.79 (t, J=53.75 Hz, 1 H);
$^{19}$F NMR (250 MHz, CHCl$_3$-d$_6$) δ ppm: 45.37 (s, COF); −117.5 (d, J=28.2 Hz); −131.6 (m);

Synthesis of 5-fluoro-3-(difluoromethyl)-1-methyl-1H-pyrazole-4-carboxylic acid (example IIe-1)

To 400 ml of a 1N sodium hydroxyde aqueous solution, was added dropwise 67.5 g of a solution (10% molar) of 3-(difluoromethyl)-5-fluoro-1-methyl-1H-pyrazole-4-carbonyl fluoride in tetrahydrothiophene 1,1-dioxide. The temperature was kept below 20° C. during the addition. After 2 hours of stirring at room temperature, the reaction mixture was carefully acidified to pH 2 with concentrated aqueous hydrochloric acid. The resulting white precipitate was filtered, washed with water, and dried to yield 6 g of 5-fluoro-3-(difluoromethyl)-1-methyl-1H-pyrazole-4-carboxylic acid as a white solid.

$^1$H NMR (400 MHz, DMSO-d$_6$) δ ppm: 3.90 (s, 3H); 7.22 (t, 1H, J$_{HF}$=53.55 Hz); 13.33 (s, 1H);

Synthesis of 5-fluoro-3-(difluoromethyl)-1-methyl-1H-pyrazole-4-carbonyl chloride (example IIf-1)

9.1 g of 5-fluoro-3-(difluoromethyl)-1-methyl-1H-pyrazole-4-carboxylic acid and 75.5 ml of thionyl chloride were refluxed for 1.5 hours. After cooling down, the reaction mixture was evaporated under vacuum to yield 10 g of 5-fluoro-3-(difluoromethyl)-1-methyl-1H-pyrazole-4-carbonyl chloride as a yellow oil.

GC-MS; observed M/z: Molecular ion: (M$^{+\cdot}$)=212; fragments: (M$^{+\cdot}$−Cl)=177 and (M$^{+\cdot}$−F)=193;

Synthesis of 5-fluoro-3-(difluoromethyl)-1-methyl-1H-pyrazole-4-carboxylic acid (IIe-1)

Step a: synthesis of 5-fluoro-3-(difluoromethyl)-1-methyl-1H-pyrazole-4-carbaldehyde (example IIg-1)

To 96.3 g (1660 mmol) of spray-dried potassium fluoride, was added a solution of 129.2 g (664 mmol) of 5-chloro-3-(difluoromethyl)-1-methyl-1H-pyrazole-4-carbaldehyde in 1000 ml of dimethylformamide. The resulting reaction mixture was stirred at 150° C. for 3 hours. The reaction mixture was cooled to room temperature and to it was added 4 L of water. The aqueous phase was extracted with ethyl acetate. The combined organic phase were washed with brine, dried over sodium sulphate and evaporated under vacuum to give the expected product.

$^1$H NMR (CD$_3$CN) δ ppm: 9.8 (1H, s), 6.88 (1H, t), 3.7 (3H, s);
$^{19}$F NMR (CD$_3$CN) δ ppm: −114.75 (2F, t), −124.06 (1F, s);

Step b: synthesis of 5-fluoro-3-(difluoromethyl)-1-methyl-1H-pyrazole-4-carboxylic acid A suspension of 79.7 g (350 mmol) of periodic acid in 640 ml absolute acetonitrile was stirred for 30 min. To this was added 56.6 g (318 mmol) of 5-fluoro-3-(difluoromethyl)-1- methyl-1H-pyrazole-4-carbaldehyde at 0° C. and a solution of 1.4 g (6 mmol) of pyridinium chlorochromate in 130 ml dry acetonitrile. The reaction mixture was stirred for 2.5 hours at room temperature. 1600 ml of ethyl acetate was added to the reaction mixture and the separated organic phase was washed consecutively with brine/water (1:1), saturated sodium metabisulfite and brine. Then the organic phase was dried with sodium sulphate, and evaporated under vacuum to give the expected product as a pale yellow solid.

Synthesis of N-cyclopropyl-3-(difluoromethyl)-5-fluoro-1-methyl-N-[2-(trimethylsilyl)benzyl]-1H-pyrazole-4-carboxamide (example 3)

To 175 mg (0.80 mmol) of N-[2-(trimethylsilyl)benzyl] cyclopropanamine in 5 ml of dry tetrahydrofurane was added 0.234 ml (1.68 mmol) of triethylamine, followed by a solution of 187 mg (0.88 mmol) of 5-fluoro-3-(difluoromethyl)-1-methyl-1H-pyrazole-4-carbonyl chloride in 3 ml of tetrahydrofurane. The reaction mixture was stirred under reflux for 3 hours. After cooling down, the reaction mixture was filtered, and the filtrate was evaporated under vacuum. The residue was dissolved in ethyl acetate/water. The aqueous phase was further extracted with ethyl acetate. The combined organic phase were dried and evaporated under vacuum to give 209 mg of the expected product.

1H NMR (400 MHz, DMSO-d6) δ ppm: 0.36 (s, 9H), 0.53 (bs, 2H) 0.64 (d, 2H), 2.86 (bs, 1H), 3.82 (bs, 3H), 4.77 (bs, 2H), 7.00 (t, J=54.06 Hz, 1H), 7.11-7.49 (m, 4H);

Synthesis of N-cyclopropyl-3-(difluoromethyl)-5-fluoro-1-methyl-N-[2-(trimethylsilyl)benzyl]-1H-pyrazole-4-carbothioamide (example 38)

A solution of 140 mg (0.31 mmol) of phosphorus pentasulfide and 500 mg (1.26 mmol) of N-cyclopropyl-3-(difluoromethyl)-5-fluoro-1-methyl-N-[2-(trimethylsilyl)benzyl]-1H-pyrazole-4-carboxamide in 20 ml of dioxane was heated at 100° C. for 2.5 hours. 2 ml of water were then added and the reaction mixture was heated at 100° C. for another 1 hour.

After cooling down, the reaction mixture was extracted with ethyl acetate. The combined organic phase were washed with an aqueous solution of sodium carbonate, dried and evaporated under vacuum. The resulting residue was purified on silica to yield 220 mg of the expected product.

1H NMR (250 MHz, DMSO-d6) δ ppm: 0.37 (s, 9H), 0.54-0.74 (m, 4H), 3.11 (bs, 1H), 3.83 (s, 3H), 5.41 (bs, 2H), 7.14 (t, J=54.40 Hz, 1H), 7.04-7.51 (m, 4H);

EXAMPLE A

In vivo Preventive Test on *Venturia inaequalis* (Apple Scab)

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous conidia suspension of the causal agent of apple scab (*Venturia inaequalis*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the untreated control, while an efficacy of 100% means that no disease is observed.

Under these conditions, good (at least 70% of disease control) to total protection (100% of disease control) is observed at a dose of 10 ppm of active ingredient with the following compounds: 1, 2, 3, 4, 5, 6, 8, 9, 10, 11, 12, 13, 14, 15, 16, 17, 18, 19, 20, 21, 22, 23, 24, 26, 28, 29, 30, 31, 32, 33, 34, 38, 39, 40, 41, 42, 43, 44, 44a, 46, 47, 48, 49, 50, 51, 52, 53, 54, 58, 61, 62, 63, 64, 65, 66, 68, 69, 70, 71, 72, 74, 75, 76, 77, 78, 80, 81, 82, 83, 84, 85, 88, 92, 95, 96, 98, 99, 101, 105, 107, 108, 109, 110, 131, 132, 133, 111, 112, 113, 114, 115, 116, 117, 118, 119, 120, 121, 122, 123, 124, 125, 126, 127, 128, 129, 130, 135, 136, 137, 138, 139, 140, 141, 142, 143, 144 and 157 according to the invention whereas weak protection (less than 30% of disease control) to no protection at all is observed at a dose of 10 ppm of active ingredient with the compounds of examples 45 disclosed in international patent WO-2006/120224, and 397 disclosed in international patent WO-2007/087906.

EXAMPLE B

In vivo Preventive Test on *Botrytis cinerea* (Beans)

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound. After the spray coating has dried on, 2 small pieces of agar covered with growth of *Botrytis cinerea* are placed on each leaf. The inoculated plants are placed in a darkened chamber at 20° C. and a relative atmospheric humidity of 100%.

2 days after the inoculation, the size of the lesions on the leaves is evaluated. 0% means an efficacy which corresponds to that of the untreated control, while an efficacy of 100% means that no disease is observed.

Under these conditions, high (at least 90% of disease control) to total protection (100% of disease control) is observed at a dose of 100 ppm of active ingredient with the following compounds: 1, 2, 3, 4, 5, 6, 9, 10, 11, 12, 13, 14, 15, 16, 17, 18, 19, 20, 21, 22, 23, 24, 25, 26, 27, 28, 29, 30, 31, 32, 33, 34, 38, 40, 41, 42, 44, 44a, 45, 46, 47, 48, 49, 50, 51, 52, 53, 54, 61, 63, 65, 68, 69, 71, 73, 75, 76, 77, 78, 81, 82, 83, 85, 88, 89, 92, 95, 96, 99, 101, 105, 107, 108, 109, 110, 111, 112, 113, 114, 115, 116, 117, 118, 119, 120, 121, 122, 123, 124, 125, 126, 127, 128, 129, 132, 133, 135, 136, 139, 138, 140, 141, 142 and 144 according to the invention whereas weak protection (less than 30% of disease control) to no protection at all is observed at a dose of 100 ppm of active ingredient with the compounds of examples 45 disclosed in international patent WO-2006/120224, and 414 disclosed in international patent WO-2007/087906.

EXAMPLE C

In vivo Curative Test on *Puccinia triticina* (Wheat)

Solvent: 49 parts by weight of n,n-dimethylacetamid
Emulsifier: 1 part by weight of alkylaryl polyglycol ether
To produce a suitable preparation of active compound, 1 part by weight of active compound or active compound combination is mixed with the stated amounts of solvent and emulsifier, and the concentrate is diluted with water to the desired concentration.

To test for curative activity, young plants are sprayed with a spore suspension of *Puccinia triticina*. The plants remain for 48 hours in an incubation cabinet at approximately 20° C. and a relative atmospheric humidity of approximately 100%.

2 days later the plants are sprayed with the preparation of active compound or active compound combination at the stated rate of application.

The plants are placed in the greenhouse at a temperature of approximately 20° C. and a relative atmospheric humidity of approximately 80%.

The test is evaluated 8 days after the inoculation. 0% means an efficacy which corresponds to that of the untreated control, while an efficacy of 100% means that no disease is observed.

Under these conditions, high (at least 95% of disease control) to total protection (100% of disease control) is observed at a dose of 500 ppm of active ingredient with the following compounds: 1, 2, 3, 4, 5, 6, 8, 9, 11, 13, 15, 21, 23, 24, 25, 28, 29, 33, 36, 37, 38, 39, 41, 42, 43, 45, 48, 49, 52, 53, 61, 63, 83, 84, 90 and 105 according to the invention whereas weak protection (less than 70% of disease control) to no protection at all is observed at a dose of 500 ppm of active ingredient with the compounds of examples 45 and 54 disclosed in international patent WO-2006/120224, and 22 disclosed in international patent WO-2009/016218 and weaker protection (less than 85% of disease control) is observed at a dose of 500 ppm of active ingredient with the compound of example 89 disclosed in international patent WO-2009/016221.

EXAMPLE D

In vivo Curative Test on *Fusarium nivale* (Wheat)

Solvent: 49 parts by weight of n,n-dimethylacetamid
Emulsifier: 1 part by weight of alkylaryl polyglycol ether
To produce a suitable preparation of active compound, 1 part by weight of active compound or active compound combination is mixed with the stated amounts of solvent and emulsifier, and the concentrate is diluted with water to the desired concentration.

To test for curative activity, young plants are sprayed with a spore suspension of *Puccinia* triticina. The plants remain for 48 hours in an incubation cabinet at approximately 20° C. and a relative atmospheric humidity of approximately 100%.

2 days later the plants are sprayed with the preparation of active compound or active compound combination at the stated rate of application.

The plants are placed in the greenhouse at a temperature of approximately 20° C. and a relative atmospheric humidity of approximately 80%.

The test is evaluated 8 days after the inoculation. 0% means an efficacy which corresponds to that of the untreated control, while an efficacy of 100% means that no disease is observed.

Under these conditions, total protection (100% of disease control) is observed at a dose of 500 ppm of active ingredient with the following compounds: 1, 2, 4, 5, 6, 8, 9, 10, 14, 15, 16, 17, 18, 20, 23, 24, 25, 28, 29, 30, 33, 36, 39, 40, 41, 42, 43, 44, 45, 46, 48, 51, 52, 53, 61, 63, 64, 80, 81, 84, 90 and 105 according to the invention whereas weak protection (less than 95% of disease control) is observed at a dose of 500 ppm of active ingredient with the compound of example 89 disclosed in international patent WO-2009/016221.

EXAMPLE E

In vivo Preventive Test on *Phakopsora pachyrhizi* (Soybean Rust)

Solvent: 28.5 parts by weight of acetone
Emulsifier: 1.5 parts by weight of polyoxyethylene alkyl phenyl ether
To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. One day after spraying, the plants are inoculated with an aqueous spore suspension of the causal agent of soybean rust (*Phakopsora pachyrhizi*). The plants are then placed in a greenhouse at approximately 20° C. and a relative atmospheric humidity of approximately 80%.

The test is evaluated 11 days after the inoculation. 0% means an efficacy which corresponds to that of the control, while an efficacy of 100% means that no disease is observed.

Under these conditions, high (at least 90% of disease control) to total protection (100% of disease control) is observed at a dose of 50 ppm of active ingredient with the following compounds: 3, 11, 12, 13, 16, 24, 25, 37, 38, 49 and 74 according to the invention whereas weak protection (less than 50% of disease control) to no protection at all is observed at a dose of 50 ppm of active ingredient with the compounds of examples 397 and 402 disclosed in international patent WO-2007/087906, 22 disclosed in international patent WO-2009/016218 and 89 disclosed in international patent WO-2009/016221 and weaker protection (less than 85% of disease control) is observed at a dose of 50 ppm of active ingredient with the compound of example 7 disclosed in international patent WO-2009/016220.

EXAMPLE F

In vivo Curative Test on *Blumeria graminis* (Wheat)

Solvent: 49 parts by weight of n,n-dimethylacetamid
Emulsifier: 1 part by weight of alkylaryl polyglycol ether
To produce a suitable preparation of active compound, 1 part by weight of active compound or active compound combination is mixed with the stated amounts of solvent and emulsifier, and the concentrate is diluted with water to the desired concentration.

To test for curative activity, young plants are dusted with spores of *Blumeria graminis* f.sp. *tritici* and placed then in a greenhouse at a temperature of approximately 18° C. and a relative atmospheric humidity of approximately 80%.

48 hours after inoculation, the plants are sprayed with the preparation of active compound or active compound combination at the stated rate of application.

After the spray coating has been dried, the plants are placed again in a greenhouse at a temperature of approximately 18° C. and a relative atmospheric humidity of approximately 80% to promote the development of mildew pustules.

The plants are placed in the greenhouse at a temperature of approximately 18° C. and a relative atmospheric humidity of approximately 80% to promote the development of mildew pustules.

The test is evaluated 7 days after the inoculation. 0% means an efficacy which corresponds to that of the untreated control, while an efficacy of 100% means that no disease is observed.

Under these conditions, good (at least 80% of disease control) to total protection (100% of disease control) is observed at a dose of 250 ppm of active ingredient with the following compounds: 1, 2, 3, 5, 6, 8, 9, 10, 11, 12, 15, 29, 30, 33, 38, 39, 46, 47, 48, 50, 51, 52, 53, 61, 68, 70 and 72 according to the invention whereas weak protection (less than 70% of disease control) to no protection at all is observed at a dose of 250 ppm of active ingredient with the compounds of examples 22 disclosed in international patent WO-2009/016218 and 89 disclosed in international patent WO-2009/016221.

EXAMPLE G

In vivo Preventive Test on *Sphaerotheca fuliginea* (Cucumber)

Solvent: 49 parts by weight of N,N-Dimethylformamide
Emulsifier: 1 part by weight of Alkylarylpolyglycolether
To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

The test is evaluated 7 days after the inoculation. 0% means an efficacy which corresponds to that of the untreated control, while an efficacy of 100% means that no disease is observed.

Under these conditions, total protection (100% of disease control) is observed at a dose of 10 ppm of active ingredient with the following compounds: 1, 2, 5, 6, 8, 10, 11, 12, 13, 14, 15, 18, 22, 23, 24, 26, 27, 29, 32, 38, 41, 44a, 47, 49, 50, 52, 54, 62, 68, 70, 72, 73, 80, 81, 82, 83, 84, 99, 101, 111, 112, 113, 115, 116, 117, 118, 119, 120, 121, 123, 124, 126, 127, 128, 130, 131, 132, 135, 136, 137, 138, 139, 141, and 157 according to the invention whereas weak protection (less than 85% of disease control) is observed at a dose of 10 ppm of active ingredient with the compounds of examples 45 disclosed in international patent WO-2006/120224 and 89 disclosed in international patent WO-2009/016221.

EXAMPLE H

In vivo Preventive Test on *Alternaria solani* (Tomato)

Solvent: 49 parts by weight of N,N-Dimethylformamide
Emulsifier: 1 part by weight of Alkylarylpolyglycolether
To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Alternaria solani*. The plants remain for one day in an incubation cabinet at approximately 22° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the untreated control while an efficacy of 100% means that no disease is observed.

Under these conditions, good (at least 70% of disease control) to total protection (100% of disease control) is observed at a dose of 500 ppm of active ingredient with the following compounds: 1, 2, 3, 4, 5, 10, 11, 12, 13, 14, 15, 16, 17, 18, 19, 21, 22b, 23, 24, 25, 27, 28, 29, 30, 31, 32, 32, 33, 34, 35, 36, 38, 39, 40, 40a, 40b, 41, 42, 43, 44, 44a, 44b, 45, 46b, 54, 55, 56, 57, 58, 59, 60, 61, 62, 64, 65, 66, 67, 68, 69, 71, 73, 74, 75, 76, 77, 78, 83, 85, 86, 87, 88, 89, 92, 93, 94, 95, 96, 97, 99, 100, 101, 102, 103, 105, 106, 107, 108, 109, 110, 111, 112, 113, 114, 115, 116, 117, 118, 119, 120, 121, 122, 123, 124, 125, 126, 127, 128, 131, 132, 133, 136, 137, 138, 139, 140, 141, 142, 143, 144 and 157.

EXAMPLE I

In vivo Preventive Test on *Leptosphaeria nodorum* (Wheat)

Solvent: 49 parts by weight of n,n-dimethylacetamid
Emulsifier: 1 part by weight of alkylaryl polyglycol ether
To produce a suitable preparation of active compound, 1 part by weight of active compound is mixed with the stated amounts of solvent and emulsifier, and the concentrate is diluted with water to the desired concentration.

To test for preventive activity, young plants are sprayed with a preparation of active compound at the stated rate of application. One day after this treatment, the plants are inoculated with an aqueous spore suspension of *Leptosphaeria nodorum*. The plants remain for 48 hours in an incubation cabinet at 22° C. and a relative atmospheric humidity of 100%. Then the plants are placed in a greenhouse at a temperature of approximately 22° C. and a relative atmospheric humidity of approximately 90%.

The test is evaluated 7-9 days after the inoculation. 0% means an efficacy which corresponds to that of the untreated control, while an efficacy of 100% means that no disease is observed.

Under these conditions, good (at least 70% of disease control) to total protection (100% of disease control) is observed at a dose of 500 ppm of active ingredient with the following compounds: 1, 2, 3, 4, 5, 6, 8, 9, 10, 11, 12, 13, 14, 15, 16, 17, 18, 19, 20, 21, 22, 22a, 22b, 23, 24, 25, 26, 27, 28, 29, 30, 31, 32, 33, 34, 38, 39, 40, 40a, 40b, 41, 42, 43, 44, 44a, 44b, 45, 46, 46a, 46b, 54, 55, 57, 58, 60, 61, 62, 63, 64, 65, 66, 67, 68, 69, 70, 71, 72, 73, 74, 75, 76, 77, 78, 80, 81, 82, 83, 84, 85, 87, 88, 89, 90, 91, 92, 95, 96, 97, 98, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 135, 136, 137, 138, 139, 140, 141 and 144.

EXAMPLE J

In vivo Preventive Test on *Puccinia recondita* (Wheat)

Solvent: 49 parts by weight of n,n-dimethylacetamid
Emulsifier: 1 part by weight of alkylaryl polyglycol ether
To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Puccinia recondita*. The plants remain for 48 hours in an incubation cabinet at 22° C. and a relative atmospheric humidity of 100%. Then the plants are placed in a greenhouse at a temperature of approximately 20° C. and a relative atmospheric humidity of approximately 80%.

The test is evaluated 7-9 days after the inoculation. 0% means an efficacy which corresponds to that of the untreated control while an efficacy of 100% means that no disease is observed.

Under these conditions, good (at least 70% of disease control) to total protection (100% of disease control) is observed at a dose of 500 ppm of active ingredient with the following compounds: 1, 2, 3, 4, 5, 6, 8, 9, 10, 11, 12, 13, 14, 15, 16, 17, 18, 19, 20, 21, 22, 22a, 23, 24, 25, 26, 27, 28, 29, 30, 31, 32, 32, 33, 34, 35, 36, 37, 38, 39, 40, 40b, 41, 42, 43, 44, 44a, 45, 46, 46a, 54, 55, 56, 57, 58, 59, 60, 61, 62, 63, 64, 65, 68, 69, 70, 71, 72, 74, 75, 76, 77, 78, 80, 81, 82, 83, 84, 84, 85, 86, 87, 88, 89, 92, 94, 95, 97, 99, 100, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 135, 136, 137, 138, 139, 140, 141, 142, 143, 144 and 157.

EXAMPLE K

In vivo Preventive Test on *Pyrenophora teres* (Barley)

Solvent: 49 parts by weight of n,n-dimethylacetamid
Emulsifier: 1 part by weight of alkylaryl polyglycol ether
To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Pyrenophora teres*. The plants remain for 48 hours in an incubation cabinet at 22° C. and a relative atmospheric humidity of 100%. Then the plants are placed in a greenhouse at a temperature of approximately 20° C. and a relative atmospheric humidity of approximately 80%.

The test is evaluated 7-9 days after the inoculation. 0% means an efficacy which corresponds to that of the untreated control while an efficacy of 100% means that no disease is observed.

Under these conditions, good (at least 70% of disease control) to total protection (100% of disease control) is observed at a dose of 500 ppm of active ingredient with the following compounds: 1, 2, 3, 4, 5, 9, 10, 11, 12, 13, 14, 15, 16, 17, 18, 19, 20, 21, 22, 22a, 22b, 23, 24, 25, 26, 27, 28, 29, 30, 31, 32, 32, 33, 34, 35, 36, 37, 38, 39, 40, 40a, 40b, 41, 42, 43, 44, 44a, 44b, 45, 46, 46a, 46b, 54, 55, 56, 57, 58, 59, 60, 61, 62, 63, 64, 65, 66, 67, 68, 69, 70, 71, 72, 73, 74, 75, 76, 77, 78, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 135, 136, 137, 138, 139, 140, 141, 142, 143, 144 and 157.

EXAMPLE L

In vivo Preventive Test on *Sphaerotheca fuliginea* (Cucumber)

Solvent: 49 parts by weight of N,N-Dimethylformamide
Emulsifier: 1 part by weight of Alkylarylpolyglycolether
To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Sphaerotheca fuliginea*. Then the plants are placed in a greenhouse at approximately 23° C. and a relative atmospheric humidity of approximately 70%.

The test is evaluated 7 days after the inoculation. 0% means an efficacy which corresponds to that of the untreated control, while an efficacy of 100% means that no disease is observed.

In this test the following compounds according to the invention showed efficacy of 70% or even higher at a concentration of 500 ppm of active ingredient.

Under these conditions, good (at least 70% of disease control) to total protection (100% of disease control) is observed at a dose of 500 ppm of active ingredient with the following compounds: 1, 2, 3, 4, 5, 6, 8, 9, 10, 11, 12, 13, 14, 15, 16, 18, 19, 20, 21, 22, 22a, 22b, 23, 24, 25, 26, 27, 28, 29, 30, 31, 32, 33, 34, 36, 38, 39, 40, 40a, 40b, 41, 42, 43, 44, 44a, 45, 46, 46a, 46b, 54, 55, 56, 58, 61, 62, 63, 64, 65, 66, 68, 69, 70, 71, 72, 73, 74, 75, 76, 77, 78, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 135, 136, 137, 138, 139, 140, 141, 142, 143, 144 and 157.

EXAMPLE M

Inhibition of Fumonisin FB1 Produced by *Fusarium proliferatum*

Compounds were tested in microtiter plates in fumonisin-inducing liquid media (0.5 g malt extract, 1 g yeast extract, 1 g bacto peptone, 20 g Fructose, 1 g $KH_2PO_4$, 0.3 g $MgSO_4 \times 7H_2O$, 0.3 g KCl, 0.05 g $ZnSO_4 \times 7H_2O$ and 0.01 g CuSO$_4$x5H$_2$O per liter) containing 0.5% DMSO, inoculated with a concentrated spore suspension of *Fusarium proliferatum* to a final concentration of 2000 spores/ml.

Plates were covered and incubated at high humidity at 20° C. for 5 days

At start and after 5 days OD measurement at OD620 multiple read per well (square: 3×3) was taken to calculate growth inhibition.

After 5 days samples of each culture medium were taken and diluted 1:1000 in 50% acetonitrile. The amounts of fumonisin FB1 of the samples were analysed per HPLC-MS/MS and results were used to calculate inhibition of FB1 production in comparison to a control without compound. HPLC-MS/MS was done with the following parameters:

Ionization mode: ESI positive

Ionspray voltage: 5500V

Spraygas Temperature: 500° C.

Declustering potential: 114V

Collision energy: 51 eV

Collision gas: $N_2$

MRM trace: 722,3>352,3; dwell time 100 ms

HPLC column: Waters Atlantis T3 (trifunctional C18 bonding, fully endcapped)

Particle size: 3 μm

Column size: 50×2 mm

Temperature: 40° C.

Solvent A: Water+0.1% HCOOH (v/v)

Solvent B: Acetonitrile+0.1% HCOOH (v/v)

Flow: 400 μL/min

Injection volume: 5 μL

Gradient:

| Time [min] | A % | B % |
|---|---|---|
| 0 | 90 | 10 |
| 2 | 5 | 95 |
| 4 | 5 | 95 |
| 4.1 | 90 | 10 |
| 9 | 90 | 10 |

Under these conditions, an activity of >80% of inhibition of Fumonisin FB1 production is observed at a dose of 50 μM of active ingredient with the following compounds: 2, 4, 6, 8, 9, 14, 15, 16, 17, 18, 19, 20, 21, 22, 23, 25, 26, 27, 28, 29, 30, 31, 32, 33, 35, 36, 40, 41, 42, 44, 45, 46, 47, 48, 49, 50, 51, 52, 53, 54, 56, 58, 60, 61, 62, 63, 65, 66 and 67 whereas weak activity (less than 55% of Fumonisin FB1 production inhibition) to no activity is observed at a dose of 50 μM of active ingredient with the compound of example 54 disclosed in international patent WO-2006/120224.

Growth inhibition of *Fusarium proliferatum* of these examples varied from 27 to 84% at 50 μM of active ingredient.

EXAMPLE N

Inhibition of Deoxynivalenol (DON) and Acetyldeoxynivalenol (Acetyl-DON) Produced by *Fusarium graminearum*

Compounds were tested in microtiter plates in DON-inducing liquid media (1 g $(NH_4)_2HPO_4$, 0.2 g $MgSO_4x7H_2O$, 3 g $KH_2PO_4$, 10 g Glycerin, 5 g NaCl and 40 g Sachharose per liter), supplemented with 10% oat extract, containing 0.5% DMSO, inoculated with a concentrated spore suspension of *Fusarium graminearum* to a final concentration of 2000 spores/ml.

The plate was covered and incubated at high humidity at 28° C. for 7 days.

At start and after 3 days OD measurement at OD620 multiple read per well (square: 3×3) was taken to calculate the growth inhibition.

After 7 days 1 volume of 84/16 acetonitrile/water was added to each well and a sample of the liquid medium was taken and diluted 1:100 in 10% acetonitrile. The amounts of DON and Acetyl-DON of the samples were analysed per HPLC-MS/MS and results were used to calculate inhibition of DON/AcDON production in comparison to a control without compound. HPLC-MS/MS was done with the following parameters:

Ionization mode: ESI negative

Ionspray voltage: −4500V

Spraygas Temperature: 500° C.

Declustering potential: −40V

Collision energy: −22 eV

Collision gas: $N_2$

MRM trace: 355,0>264,9; dwell time 150 ms

HPLC column: Waters Atlantis T3 (trifunctional C18 bonding, fully endcapped)

Particle size: 3 μm

Column size: 50×2 mm

Temperature: 40° C.

Solvent A: Water/2.5 mM $NH_4OAc$+0.05% $CH_3COOH$ (v/v)

Solvent B: Methanol/2.5 mM $NH_4OAc$+0.05% $CH_3COOH$ (v/v)

Flow: 400 μL/min

Injection volume: 11 μL

Gradient:

| Time [min] | A % | B % |
|---|---|---|
| 0 | 100 | 0 |
| 0.75 | 100 | 0 |
| 1.5 | 5 | 95 |
| 4 | 5 | 95 |
| 5 | 100 | 0 |
| 10 | 100 | 0 |

Under these conditions, an activity of >80% of inhibition of DON/Acetyl-DON production is observed at a dose of 50 μM of active ingredient with the following compounds: 18, 22, 26, 40, 44, 46, 47, 48, 50, 51, 54, 58, 62, 63, 65 and 66.

Growth inhibition of *Fusarium graminearum* of these examples varied from 14 to 100% at 50 μM of active ingredient.

EXAMPLE O

Inhibition of Aflatoxines Produced by *Aspercqillus parasiticus*

Compounds were tested in microtiter plates (96 well black flat and transparent bottom) in Aflatoxin-inducing liquid media (20 g sucrose, yeast extract 4 g, $KH_2PO_4$ 1 g, and $MgSO_4$ $7H_2O$ 0.5 g per liter), supplemented with 20 mM of Cavasol (hydroxypropyl-beta-cyclodextrin) and containing 1% of DMSO. The assay is started by inoculating the medium with a concentrated spore suspension of *Aspergillus parasiticus* at a final concentration of 1000 spores/ml.

The plate was covered and incubated at 20° C. for 7 days.

After 7 days of culture, OD measurement at $OD_{620nm}$ with multiple read per well (circle: 4×4) was taken with an Infinite 1000 (Tecan) to calculate the growth inhibition. In the same time bottom fluorescence measurement at $Em_{360nm}$ and $Ex_{426nm}$ with multiple read per well (square: 3×3) was taken to calculate inhibition of aflatoxin formation.

Under these conditions, an activity of >80% of inhibition of aflatoxines production is observed at a dose of 50 µM of active ingredient with the following compounds: 1, 2, 3, 6, 8, 9, 11, 13, 14, 15, 16, 17, 18, 19, 20, 21, 22, 22, 25, 26, 27, 28, 29, 30, 31, 33, 34, 35, 36, 38, 39, 40, 42, 43, 45, 46, 47, 48, 49, 50, 51, 52, 53, 54, 55, 56, 57, 58, 59, 60, 61, 62, 63, 65 and 66.

Growth inhibition of *Fusarium graminearum* of these examples was also >80% at 50 µM of active ingredient.

EXAMPLE P

Injection Test on *Boophilus microplus*

Solvent: dimethyl sulfoxide

To produce a suitable preparation of active compound, 10 mg of active compound are dissolved in 0.5 ml solvent, and the concentrate is diluted with solvent to the desired concentration. Five adult engorged female ticks (*Boophilus microplus*) are injected with 1 µl compound solution into the abdomen. Ticks are transferred into replica plates and incubated in a climate chamber for a period of time. Egg deposition of fertile eggs is monitored.

After 7 days, mortality in % is determined. 100% means that all eggs are infertile; 0% means that all eggs are fertile.

In this test, the following compounds from the preparation examples showed good activity of >80% at application rate of 20 µg of active ingredient/animal: 4, 5, 6, 7, 12, 29 and 30.

EXAMPLE Q

Spray Application Test on *Tetranychus urticae*

Solvent: 78.0 parts by weight acetone
1.5 parts by weight dimethylformamide
Emulsifier: 0.5 parts by weight alkylarylpolyglcolether To produce a suitable preparation of active compound, 1 part by weight of active compound is mixed with the stated amount of solvent and emulsifier, and the concentrate is diluted with emulsifier-containing water to the desired concentration. French beans (*Phaseolus vulgaris*) which are heavily infested with all stages of the two spotted spidermite (*Tetranychus urticae*), are sprayed with a preparation of the active ingredient at the desired concentration.

After 6 days, mortality in % is determined. 100% means that all spider mites have been killed and 0% means that none of the spider mites have been killed.

In this test, the following compounds from the preparation examples showed good activity of >80% at application rate of 500 g of active ingredient /ha: 1, 5, 6, 30 and 40.

EXAMPLE R

Test on *Meloidocyne ingognita*

Solvent: 80.0 parts by weight of acetone

To produce a suitable preparation of active compound, 1 part by weight of active compound is mixed with the stated amount of solvent, and the concentrate is diluted with emulsifier-containing water to the desired concentration.

Vessels are filled with sand, a solution of the active ingredient, a suspension containing eggs and larvae of *Meloidogyne incognita* and salad seeds. The salade seeds germinate and the seedlings grow. Galls develop in the roots.

After 14 days the nematicidal activity is determined on the basis of the percentage of gall formation. 100% means that no galls were found; 0% means that the number of galls found on the roots of the treated plants was equal to that in untreated control plants.

In this test, the following compound from the preparation examples showed good activity of >80% at application rate of 20 ppm of active ingredient: 6.

Example 45 disclosed in international patent WO-2006/120224 correspond to N-{[3-chloro-5-(trifluoromethyl)pyridin-2-yl]methyl}-N-cyclopropyl-5-fluoro-1,3-dimethyl-1H-pyrazole-4-carboxamide.

Example 54 disclosed in international patent WO-2006/120224 correspond to N-{[3-chloro-5-(trifluoromethyl)pyridin-2-yl]methyl}-N-cyclopropyl-3-(difluoromethyl)-5-fluoro-1-methyl-1H-pyrazole-4-carboxamide.

Example 397 disclosed in international patent WO-2007/087906 corresponds to N-[2-chloro-6-(trifluoromethyl)benzyl]-N-cyclopropyl-5-fluoro-1,3-dimethyl-1H-pyrazole-4-carboxamide.

Example 402 disclosed in international patent WO-2007/087906 corresponds to N-cyclopropyl-5-fluoro-N-(2-iodobenzyl)-1,3-dimethyl-1H-pyrazole-4-carboxamide.

Example 414 disclosed in international patent WO-2007/087906 corresponds to N-cyclopropyl-N-[1-(3,5-dichlorophenyl)ethyl]-5-fluoro-1,3-dimethyl-1H-pyrazole-4-carboxamide.

Example 89 disclosed in international patent WO-2009/016221 corresponds to N-cyclopropyl-3-(difluoromethyl)-5-fluoro-1-methyl-N-[1-(1-naphthyl)ethyl]-1H-pyrazole-4-carboxamide.

Example 22 disclosed in international patent WO-2009/016218 corresponds to N-cyclopropyl-5-fluoro-N-(6-isopropoxy-1,2,3,4-tetrahydronaphthalen-1-yl)-1,3-dimethyl-1H-pyrazole-4-carboxamide.

Example 7 disclosed in international patent WO-2009/016220 corresponds to N-cyclopropyl-5-fluoro-1,3-dimethyl-N-[2-(trimethylsilyl)benzyl]-1H-pyrazole-4-carbothioamide.

These results show that the compounds according to the invention have a much better biological activity than the structurally closest compounds disclosed in WO-2006/120224, WO-2007/087906, WO-2009/016218, WO-2009/016220 and WO-2009/016221.

The invention claimed is:

1. A method for the preparation of a compound of the formula

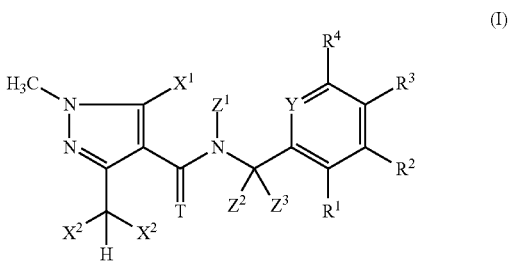

according to the following scheme:

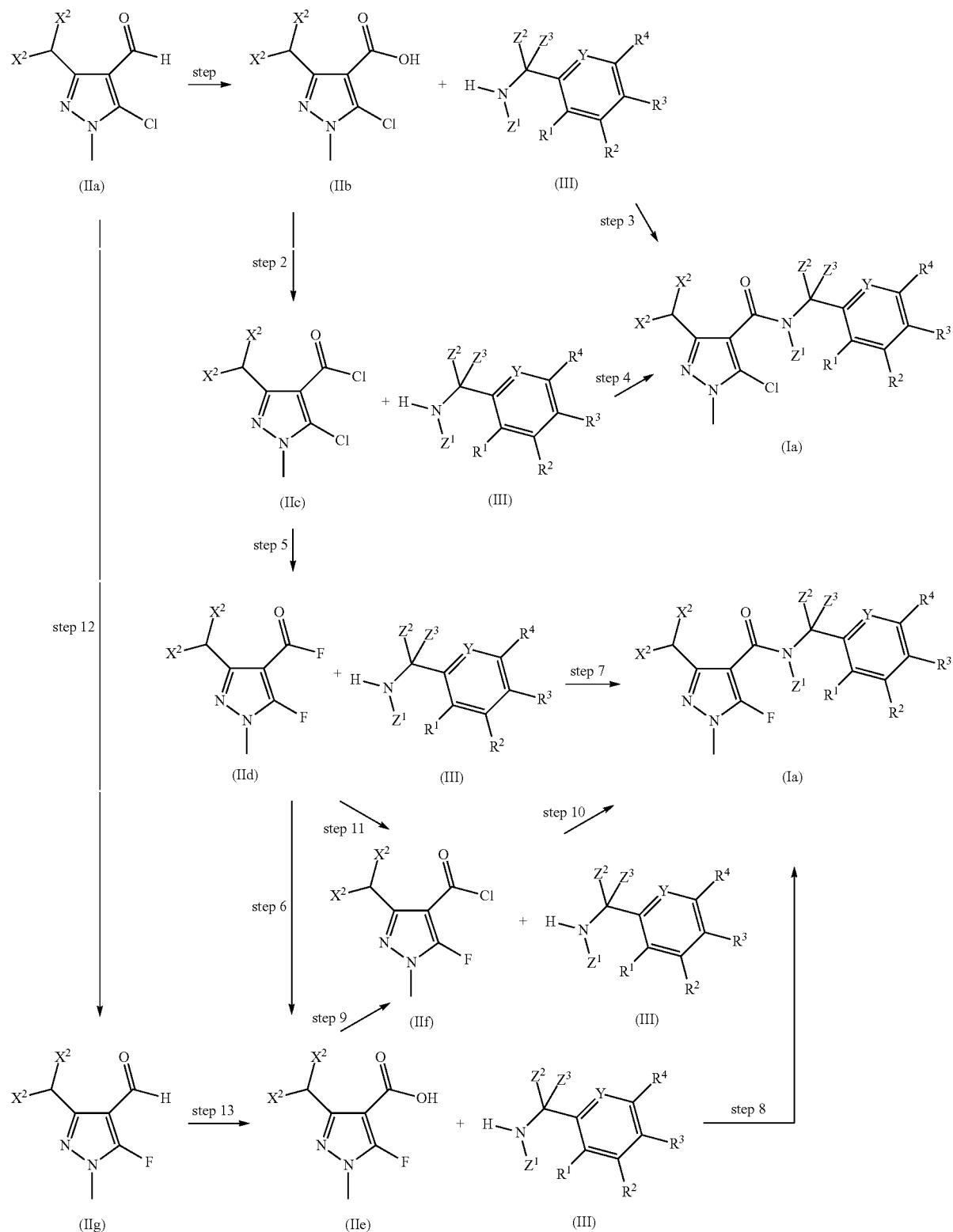

wherein:
  Y is selected from the group consisting of CR$^5$ and nitrogen;
  T is selected from the group consisting of sulfur and oxygen;

X$^1$ and X$^2$ are independently selected from the group consisting of a chlorine atom and a fluorine atom;
Z$^1$ is selected from the group consisting of a non substituted cyclopropyl and a cyclopropyl substituted by up to 2 atoms or groups independently selected from the group consisting of halogen; cyano; $C_1$-$C_8$-alkyl; and $C_1$-$C_8$-halogenoalkyl comprising up to 9 halogen atoms which can be the same or different;

$Z^2$ and $Z^3$, which can be the same or different, represent a hydrogen atom; substituted or non substituted $C_1$-$C_8$-alkyl; substituted or non substituted $C_2$-$C_8$-alkenyl; substituted or non substituted $C_2$-$C_8$-alkynyl; cyano; isonitrile; nitro; a halogen atom; substituted or non substituted $C_1$-$C_8$-alkoxy; substituted or non substituted $C_2$-$C_8$-alkenyloxy; substituted or non substituted $C_2$-$C_8$-alkynyloxy; substituted or non substituted $C_3$-$C_7$-cycloalkyl; substituted or non substituted $C_1$-$C_8$-alkylsulfanyl; substituted or non substituted $C_1$-$C_8$-alkylsulfonyl; substituted or non substituted $C_1$-$C_8$-alkylsulfinyl; amino; substituted or non substituted $C_1$-$C_8$-alkylamino; substituted or non substituted di-$C_1$-$C_8$-alkylamino; substituted or non substituted $C_1$-$C_8$-alkoxycarbonyl; substituted or non substituted $C_1$-$C_8$-alkylcarbamoyl; substituted or non substituted di-$C_1$-$C_8$-alkylcarbamoyl; or substituted or non substituted N—$C_1$-$C_8$-alkyl-$C_1$-$C_8$-alkoxycarbamoyl; or $Z^3$ and $R^1$ together with the consecutive carbon atoms to which they are linked form a substituted or non substituted 5-, 6- or 7-membered, partly saturated, carbo- or heterocycle comprising up to 3 heteroatoms and $Z^2$ is as herein described; or $Z^2$ and $Z^3$ together with the carbon atom to which they are linked form a substituted or non substituted $C_3$-$C_7$ cycloalkyl;

$R^1$, $R^2$, $R^3$, $R^4$ and $R^5$ are independently selected from the group consisting of hydrogen; halogen; nitro; cyano; isonitrile; hydroxyl; sulfanyl; amino; pentafluoro-$\lambda^6$-sulfanyl; substituted or non substituted $C_1$-$C_8$-alkyl; $C_1$-$C_8$-halogenoalkyl comprising up to 9 halogen atoms which can be the same or different; substituted or non substituted $C_1$-$C_8$-alkylamino; substituted or non substituted di-$C_1$-$C_8$-alkylamino; substituted or non substituted $C_1$-$C_8$-alkoxy; $C_1$-$C_8$-halogenoalkoxy comprising up to 9 halogen atoms which can be the same or different; $C_1$-$C_8$-alkoxy-$C_1$-$C_8$-alkyl; substituted or non substituted $C_1$-$C_8$-alkylsulfanyl; $C_1$-$C_8$-halogenoalkylsulfanyl comprising up to 9 halogen atoms which can be the same or different; substituted or non substituted $C_2$-$C_8$-alkenyl; $C_2$-$C_8$-halogenoalkenyl comprising up to 9 halogen atoms which can be the same or different; substituted or non substituted $C_2$-$C_8$-alkynyl; $C_2$-$C_8$-halogenoalkynyl comprising up to 9 halogen atoms which can be the same or different; substituted or non substituted $C_2$-$C_8$-alkenyloxy; $C_2$-$C_8$-halogenoalkenyloxy comprising up to 9 halogen atoms which can be the same or different; substituted or non substituted $C_2$-$C_8$-alkynyloxy; $C_2$-$C_8$-halogenoalkynyloxy comprising up to 9 halogen atoms which can be the same or different; substituted or non substituted $C_3$-$C_7$-cycloalkyl; $C_3$-$C_7$-halogenocycloalkyl comprising up to 9 halogen atoms which can be the same or different; substituted or non substituted $C_3$-$C_7$-cycloalkyl-$C_1$-$C_8$-alkyl; substituted or non substituted $C_3$-$C_7$-cycloalkyl-$C_2$-$C_8$-alkenyl; substituted or non substituted $C_3$-$C_7$-cycloalkyl-$C_2$-$C_8$-alkynyl; substituted or non substituted $C_3$-$C_7$-cycloalkyl-$C_3$-$C_7$-cycloalkyl; substituted or non substituted $C_1$-$C_8$-alkyl-$C_3$-$C_7$-cycloalkyl; formyl; formyloxy; formylamino; carboxy; carbamoyl; N-hydroxycarbamoyl; carbamate; (hydroxyimino)-$C_1$-$C_8$-alkyl; substituted or non substituted $C_1$-$C_8$-alkylcarbonyl; $C_1$-$C_8$-halogenoalkylcarbonyl comprising up to 9 halogen atoms which can be the same or different; substituted or non substituted $C_1$-$C_8$-alkylcarbamoyl; substituted or non substituted di-$C_1$-$C_8$-alkylcarbamoyl; N-(substituted or non substituted $C_1$-$C_8$-alkyloxy)carbamoyl; substituted or non substituted $C_1$-$C_8$-alkoxycarbamoyl; N-(substituted or non substituted $C_1$-$C_8$-alkyl)-(substituted or non substituted $C_1$-$C_8$-alkoxy)-carbamoyl; substituted or non substituted $C_1$-$C_8$-alkoxycarbonyl; $C_1$-$C_8$-halogenoalkoxycarbonyl comprising up to 9 halogen atoms which can be the same or different; substituted or non substituted $C_1$-$C_8$alkylaminocarbonyl; di-substituted or non substituted $C_1$-$C_8$-alkylaminocarbonyl; substituted or non substituted $C_1$-$C_8$-alkylcarbonyloxy; $C_1$-$C_8$-halogenoalkylcarbonyloxy comprising up to 9 halogen atoms which can be the same or different; substituted or non substituted $C_1$-$C_8$-lkylcarbonylamino; $C_1$-$C_8$-halogenoalkylcarbonylamino comprising up to 9 halogen atoms which can be the same or different; substituted or non substituted $C_1$-$C_8$-alkylaminocarbonyloxy; substituted or non substituted di-$C_1$-$C_8$alkylaminocarbonyloxy; substituted or non substituted $C_1$-$C_8$-alkyloxycarbonyloxy; substituted or non substituted $C_1$-$C_8$-alkylsulfinyl; $C_1$-$C_8$-halogenoalkylsulfinyl comprising up to 9 halogen atoms which can be the same or different; substituted or non substituted $C_1$-$C_8$-alkylsulfonyl; $C_1$-$C_8$-halogenoalkylsulfonyl comprising up to 9 halogen atoms which can be the same or different; substituted or non substituted $C_1$-$C_8$-alkoxyimino; ($C_1$-$C_8$-alkoxyimino)-$C_1$-$C_8$-alkyl; substituted or non substituted ($C_1$-$C_8$-alkenyloxyimino)-$C_1$-$C_8$-alkyl; ($C_1$-$C_8$-alkynyloxyimino)-$C_1$-$C_8$-alkyl; a (benzyloxyimino)-$C_1$-$C_8$-alkyl; tri(substituted or non substituted $C_1$-$C_8$-alkyl)silyl; tri(substituted or non substituted $C_1$-$C_8$-alkyl)silyl-$C_1$-$C_8$-alkyl; benzyloxy which can be substituted by up to 5 groups Q; benzylsulfanyl which can be substituted by up to 5 groups Q; benzylamino which can be substituted by up to 5 groups Q; aryl which can be substituted by up to 7 groups Q; aryloxy which can be substituted by up to 7 groups Q; arylamino which can be substituted by up to 7 groups Q; arylsulfanyl which can be substituted by up to 7 groups Q; aryl-$C_1$-$C_8$-alkyl which can be substituted by up to 7 groups Q; aryl-$C_2$-$C_8$-alkenyl which can be substituted by up to 7 groups Q; aryl-$C_2$-$C_8$-alkynyl which can be substituted by up to 7 groups Q; pyridinyl which can be substituted by up to 4 groups Q; pyridinyloxy which can be substituted by up to 4 groups Q; and aryl-$C_3$-$C_7$-cycloalkyl which can be substituted by up to 7 groups Q; or Two vicinal substituents R together with the consecutive carbon atoms to which they are linked form a substituted or non substituted 5- or 6-membered, saturated, carbo- or heterocycle comprising up to 3 heteroatoms and the other substituents R are as herein-described; or $R^1$ and $Z^3$ together with the consecutive carbon atoms to which they are linked form a substituted or non substituted 5-, 6- or 7-membered, partly saturated, carbo- or heterocycle comprising up to 3 heteroatoms, and $R^2$ to $R^5$ are as herein-described; and each Q is independently selected from the group consisting of halogen; cyano; nitro; $C_1$-$C_8$-alkyl; $C_1$-$C_8$alkoxy; $C_1$-$C_8$-alkylsulfanyl; $C_1$-$C_8$-halogenoalkyl comprising up to 9 halogen atoms which can be the same or different; $C_1$-$C_8$-halogenoalkoxy comprising up to 9 halogen atoms which can be the same or different; and tri($C_1$-$C_8$)alkylsilyl or tri($C_1$-$C_8$)alkylsilyl-$C_1$-$C_8$-alkyl;

with the proviso that when Y is nitrogen, and T is oxygen, and $Z^1$ is a cyclopropyl group, and $R^1$ is a chlorine atom, and $R^3$ is a trifluoromethyl group, and $R^2$ and $R^4$ are hydrogen, then a least one of the substituents $Z^2$ or $Z^3$ is not a hydrogen atom.

2. The method of claim 1 wherein wherein Y is $CR^5$.
3. The method of claim 1 wherein Y is nitrogen.
4. The method of claim 1 wherein T is oxygen.
5. The method of claim 1 wherein $X^1$ is a fluorine atom.
6. The method of claim 1 wherein $X^2$ is a fluorine atom.
7. The method of claim 1 wherein $Z^1$ is a non substituted cyclopropyl.
8. The method of claim 1 wherein $Z^2$ and $Z^3$ are independently selected from the group consisting of hydrogen atom and methyl.
9. The method of claim 8 wherein $Z^2$ is hydrogen.
10. The method of claim 1 wherein $R^1$, $R^2$, $R^3$, $R^4$ and $R^5$ are independently selected from the group consisting of hydrogen; halogen; substituted or non substituted $C_1$-$C_8$-alkyl; $C_1$-$C_8$-halogenoalkyl comprising up to 9 halogen atoms which can be the same or different; substituted or non substituted $C_3$-$C_7$-cycloalkyl; tri($C_1$-$C_8$-alkyl)silyl; and substituted or non substituted $C_1$-$C_8$alkylsulfanyl.
11. The method of claim 1 wherein $R^1$ is selected from the group consisting of halogen; $C_1$-$C_8$-alkyl; $C_1$-$C_8$-halogenoalkyl comprising up to 9 halogen atoms which can be the same or different; $C_3$-$C_7$-cycloalkyl; tri($C_1$-$C_8$-alkyl)silyl; and $C_1$-$C_8$-halogenoalkylsulfanyl comprising up to 9 halogen atoms which can be the same or different.
12. The method of claim 1 wherein $R^1$ and $R^5$ are independently selected from the group consisting of halogen; $C_1$-$C_8$-alkyl; $C_1$-$C_8$-halogenoalkyl comprising up to 9 halogen atoms which can be the same or different; $C_3$-$C_7$-cycloalkyl; tri($C_1$-$C_8$-alkyl)silyl; and $C_1$-$C_8$-halogenoalkylsulfanyl comprising up to 9 halogen atoms which can be the same or different.
13. The method of claim 1 wherein the compound of formula (IIb) is

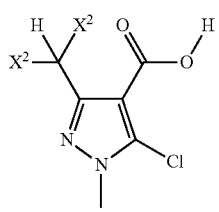

(IIb)

wherein $X^2$ is selected from the group consisting of chlorine and fluorine.

14. The method of claim 1 wherein the compound of formula (IIc) is

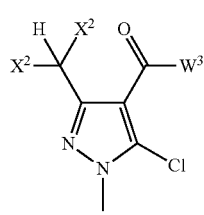

(IIc)

wherein $X^2$ is selected from the group consisting of chlorine and fluorine; and
$W^3$ is halogen.

15. The method of claim 1 wherein the compound of formula (IId) is

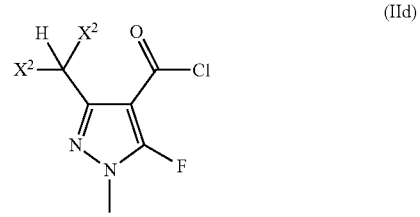

(IId)

wherein $X^2$ is selected from the group consisting of chlorine and fluorine.

16. The method of claim 1 wherein the compound of formula (IIe) is

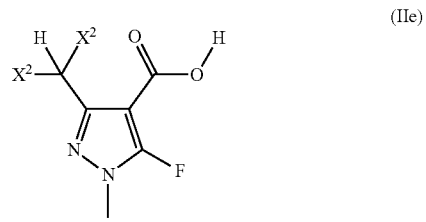

(IIe)

wherein $X^2$ is selected from the group consisting of chlorine and fluorine.

17. The method of claim 1 wherein the compound of formula (IIf) is

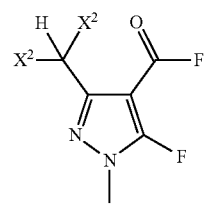

(IIf)

wherein $X^2$ is selected from the group consisting of chlorine and fluorine.

18. The method of claim 1 wherein the compound of formula (IIg) is

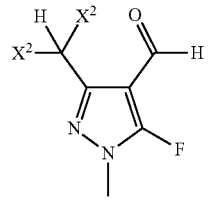

(IIg)

wherein $X^2$ is selected from the group consisting of chlorine and fluorine.

* * * * *